United States Patent [19]
Sun et al.

[11] Patent Number: 6,122,536
[45] Date of Patent: Sep. 19, 2000

[54] IMPLANTABLE SENSOR AND SYSTEM FOR MEASUREMENT AND CONTROL OF BLOOD CONSTITUENT LEVELS

[75] Inventors: Xiaoguong Sun, King of Prussia; Jeffrey I. Joseph, Penn Valley; Katherine D. Crothall, Gladwyne, all of Pa.

[73] Assignee: Animas Corporation, Malvern, Pa.

[21] Appl. No.: 08/981,860

[22] PCT Filed: Jul. 8, 1996

[86] PCT No.: PCT/US96/11435

§ 371 Date: Jun. 23, 1998

§ 102(e) Date: Jun. 23, 1998

[87] PCT Pub. No.: WO97/01986

PCT Pub. Date: Jan. 23, 1997

(Under 37 CFR 1.47)

Related U.S. Application Data

[63] Continuation-in-part of application No. 08/500,388, Jul. 6, 1995, Pat. No. 5,995,860.

[51] Int. Cl.$^7$ .............................. A61B 5/00; A61M 5/142
[52] U.S. Cl. ...................... 600/341; 600/341; 600/317; 600/322; 604/891.1; 607/22
[58] Field of Search ..................................... 600/310, 322, 600/323, 326, 327, 339, 340, 341; 356/39; 604/50, 66, 67, 890.1, 891.1; 607/22

[56] References Cited

U.S. PATENT DOCUMENTS

| | | |
|---|---|---|
| 3,837,339 | 9/1974 | Aisenbert et al. . |
| 4,013,074 | 3/1977 | Siposs . |
| 4,073,292 | 2/1978 | Edelman . |
| 4,398,908 | 8/1983 | Siposs . |
| 4,435,173 | 3/1984 | Siposs et al. . |
| 4,538,616 | 9/1985 | Rogoff . |
| 4,621,643 | 11/1986 | New, Jr. et al. . |
| 4,633,878 | 1/1987 | Bombardieri . |
| 4,679,562 | 7/1987 | Luksha . |
| 4,704,029 | 11/1987 | Van Heuvelen . |
| 4,807,629 | 2/1989 | Baudino et al. . |

(List continued on next page.)

FOREIGN PATENT DOCUMENTS

| | | |
|---|---|---|
| 4-15046 | 1/1992 | Japan . |
| 92/11801 | 7/1992 | WIPO . |

OTHER PUBLICATIONS

Rebrin, A., et al., Automated Feedback Control of Subcutaneous Glucose Concentraction in Diabetic Dogs, *Diabetologia*, vol. 32, pp. 573–576, 1989.

Koudelka, M., et al., In–Vivo Behaviour of Hypodermically Implanted Microfabricated Glucose Sensors, *Biosensors & Bioelectronics*, vol. 6, pp 31–36, 1991.

(List continued on next page.)

*Primary Examiner*—Eric F. Winakur
*Attorney, Agent, or Firm*—Akin, Gump, Strauss, Hauer & Feld, L.L.P.

[57] ABSTRACT

This invention is an implantable sensor and system capable of measuring, controlling, monitoring and reporting blood constituent levels. The implantable sensor for sensing in vivo the level of at least one blood constituent in mammalian vascular tissue having at least one source of radiation from infrared through visible light, arranged to direct the radiation at the tissue where it is affected by interaction with the tissue, and at least one detector. The invention also encompasses a device for measuring and controlling the level of a blood constituent, such as glucose or oxygen, and includes an implantable infrared source module for generating an output signal representative of the sensed infrared radiation. The system includes a processor module responsive to the output signal which performs spectral analysis of the output signal and generates a control signal. The system further includes other devices for dispensing doses of medications or controlling organ function in response to the control signal.

28 Claims, 11 Drawing Sheets

U.S. PATENT DOCUMENTS

| | | |
|---|---|---|
| 4,822,336 | 4/1989 | DiTraglia . |
| 4,825,879 | 5/1989 | Tan et al. . |
| 4,830,488 | 5/1989 | Heinze et al. . |
| 4,865,038 | 9/1989 | Rich et al. . |
| 4,890,621 | 1/1990 | Hakky . |
| 4,979,509 | 12/1990 | Hakky . |
| 5,054,487 | 10/1991 | Clarke . |
| 5,101,814 | 4/1992 | Palti . |
| 5,127,406 | 7/1992 | Yamaguchi . |
| 5,179,951 | 1/1993 | Knudson . |
| 5,190,041 | 3/1993 | Palti . |
| 5,204,532 | 4/1993 | Rosenthal . |
| 5,305,745 | 4/1994 | Zacouto . |
| 5,353,792 | 10/1994 | Lubbers et al. . |
| 5,361,759 | 11/1994 | Genevier et al. . |
| 5,368,028 | 11/1994 | Palti . |
| 5,474,552 | 12/1995 | Palti . |
| 5,598,841 | 2/1997 | Taniji et al. . |
| 5,713,939 | 2/1998 | Nedungadi et al. ....................... 607/33 |

OTHER PUBLICATIONS

Fischer et al., "Assessment of subcutaneous glucose concentration: validation of the wick technique as a reference for implanted electrochemical sensors in normal and diabetic dogs", Diabetologia, vol. 30, pp. 940–945. Date 1987.

Pickup, J.C. et al., "In vivo molecular sensing in diabetes mellitus: an implantable glucose sensor with direct electron transfer", Diabetologia, vol. 32, pp. 213–217. Date 1989.

Zeller, H., et al., "Blood glucose measurement by infrared spectroscopy", *International Journal of Artificial Organs*, vol. 12, p. 129 (1989).

Arnold, M.A., et al., Determination of physiological levels of glucose in an aqueous matrix with digitally filtered Fourier Transformation Neat–Infrared Spectra, *Analytical Chemistry*, vol. 62, pp. 1457–1464 (1990).

Shichiri, M., et al., An artificial endocrin pancreas—problems awaiting solution for long term clinical applications of a glucose sensor, *Frontiers of Medical and Biological Engineering*, vol. 3, 283 (1991).

Henise, H.M., et al., Noninvasive blood glucose sensors based on near–infrared spectroscopy, *Artificial Organs*, vol. 18, 439 (1994).

Heise, H.M., et al., Multivariate Determination of Glucose in Whole Blood by Attenuated Total Reflection Infrared Spectroscopy, *Analytical Chemistry*, vol. 61 No. 18, Sep. 15, 1989.

Johnson, K.W., et al., In Vivo Evaluation of an Electroenzymatic Glucose Sensor Implanted in Subcutaneous Tissue, *Biosensors & Bioelectronics*, vol. 7, pp 709–714, 1992.

Miyazawa, T., Characteristic Infrared Bands of Monosubstituted Amides, *The Journal of Chemical Physics*, vol. 24, No. 2, Feb. 1956.

Abe, T., et al., Characterization of Glucose Microsensors for Intracellular Measurements, *Anal. Chem. 1992*, vol. 64, pp 2160–2163, 1992.

Conway, J., Ph.D., A New Approach for the Estimation of Body Composition: Infrared Interactance, *The American Journal of Clinical Nutrition 40*: Dec., 1984, pp 1123–1130.

Abel, P., et al., The $GOD-H_2O_2$–Electrode as an Approach to Implantable Glucose Sensors. (no date available).

Lanza, E., Determination of Moisture, Protein, Fat, and Calories in Raw Pork and Beef by Near Infrared Spectroscopy.

Tallagrand, T., et al., Evaluation of Implantable Glucose Enzyme–Based Sensors with Extracorporeal Blood Shunt, 1988. (best copy available).

Mathlouthi, M., Laser–Raman Spectra of D–Glucose and Sucrose in Aqueous Solution, *Carbohydrate Research*, vol. 81, (1980) pp. 203–212.

Gough, D.A., Issues Related to In Vitro Operation of Potentially Implantable Enzyme Electrode Glucose Sensors. (no date available).

Stewart, R., et al., Infrared Analysis of Serum Protein from One Hundred and Five Hundred Adults, *J. Lab. & Clin. Med.* Sep. 1960, vol. 56, No. 3.

Clark, L.C., et al., Long–Term Stability of Electroenzymatic Glucose Sensors Implanted in Mice, *Trans Am Soc Artif Intern Organs*, vol. 34, 1988.

Ertefai, S., et al., Physiological Preparation for Studying the Response of Subcutaneously Implanted Glucose and Oxygen Sensors, *Biomed Engineering*, vol. 11, Sep. 1989.

Marback, R., et al., On the Efficiency of Algorithms for Multivariate Linear Calibration used in Analytical Spectroscopy, *Trends in Analytical Chemistry*, vol. 11, No. 8, 1992.

Chang, K., et al., Validation and Bioengineering Aspects of an Implantable Glucose Sensor. (no date available).

Heise, H.M., et al, Multivariate Detrmination of Blood Substrates in Human Plasma, *International Conference on Fourier Transform Spectroscopy* (1991).

Pickup, J.C., et al., Progress Towards In Vivo Glucose Sensing with a Ferrocene–Mediated Amperometric Enzyme Electrode. (no date available).

Bauer, B., et al., Monitoring of Glucose in Biological Fluids by Fourier–Transform Infrared Spectrometry with a Cylindrical Internal Reflectance Cell, *Analytical Chimica Acta*, (1987).

Guyton, J.R., et al., The Development of an Implantable electrochemical Glucose Sensor: Response to Glucose in Bovine Serum Ultrafiltrate. (no date available).

Haaland, D., et al., Reagentless Near–Infrared Determination of Glucose in Whole Blood Using Multivariate Calibration, *Applied Spectroscopy*, vol. 46, No. 10, 1992.

Cammann K. Implantable Electrochemical Glucose Sensors—State of the Art. (no date available).

Hopkinson, J., et al., Applications of Attenuated Total Reflection in the Infrared Analysis of Carbohydrates and Biological Whole Cell Samples in Aqueous Solution, *Analyst*, vol. 112, Apr. 1987.

Xie, S., Ph.D., et al., Performances of Potentially Implantable. Rechargeable Glucose Sensors In Vitro at Body Temperature, *Biomedical Instrumentation & Technology*, Sep./Oct. 1991 pp. 393–399.

Kaiser, N., Communication, *Transaction on Biomedical Engineering*, vol. BE–26, No. 10, Oct. 1979.

Wilson, G., et al., Progress toward the Development of an Implantable Sensor for Glucose, *Clinical Chemistry*, vol. 38, No. 9, 1992.

Guyton, A., M.D., Insulin, Glucagon, and Diabetes Mellitus, *Textbook of Medical Physiology*, 8th Edition.

Moatti–Sirat, D., et al., Towards Continuous Glucose Monitoring In Vivo Evaluation of a Miniaturized Glucose Sensor Implanted for Several Days in Rat Subcutaneous Tissue, *Diabetology*, vol. 35, pp. 224–230, 1992.

Velho, G., et al., Strategies for Calibrating a Subcutaneous Glucose Sensor, *Biomed. Biochimica Acta* (1989).

Armour, J.C., et al., Application of Chronic Intravascular Blood Glucose Sensor in Dogs, *Diabetes*, Dec. 1990.

Velho, G., et al., Determination of Peritoneal Glucose Kinetics in Rats: Implications for the Peritoneal Implantation of Closed–Loop Insulin Delivery Systems, *Diabetologia* (1989) vol. 32, pp. 331–336.

von Woedtke, T., et al., Implantable Glucose Sensors: Comparison between In Vitro and In Vivo 24 Kinetics, *The International Journal or Artificial Organs*, vol. 14, No. 8, pp 473–481, 1991.

Kolendorf, K., et al., Determination of 24–Hour Insulin Infusion Pattern by an Artificial Endocrine Pancreas for Intraveneous Insulin Infusion with a Miniature Pump, *Horm. Metab. Res.* vol. 13, pp 245–249 (1981).

Poitout, V., et al., In Vitro and In Vivo Evaluation in Dogs of a Miniaturized Glucose Sensor. (no date available).

Goetz, F., Conference on Beta Cell Function, Transplantation, and Implantable Glucose Sensors: A Summary, *Metabolism*, vol. 23, No. 9, Sep., 1974.

Rebrin, A., et al., Automated Feedback Control of Subcutaneous Glucose Conentration in Diabetic Dogs, *Diabetologia*, vol. 32, pp. 573–576, 1989.

Hollander, P.M.D., et al. Diabetes in pregnancy, *Park Nicollet Medical Center*.

Fischer, U. et al., A Membrane Combination for Implantable Glucose Sensors. Measurement in Undiluted Biological Fluids, *Trans Am Soc Artif Intern Organs*, vol. 28, 1982.

Robinson, R.M., et al., Noninvasive Glucose Monitoring in Diabetic Patients: A Preliminary Evaluation, *Clinical Chemistry*, vol. 38, No. 9, 1992.

Woedtke, et al., In Situ Calibration of Implanted Electrochemical Glucose Sensors, *Biomed Biochim Acta*, vol. 48, 1989.

Schultz, J.S., et al., Affinity Sensor: A New Technique for Developing Implantable Sensors for Glucose and Other Metabolites, *Diabetes Care*, vol. 5, No. 3, May–Jun. 1982.

Pickup, J.C., et al., Potentially–Implantable, Amperometric Glucose sensors with Medical Electron Transfer: Improving the Operating Stability, *Biosensors* (1989).

Clark, L.C., Long–Term Implantation of Voltammetric Oxidase/Peroxide Glucose Sensors in the Rat Peritoneum, *Methods in Enzymology*, vol. 137.

Drake, R.F., et al., In Vitro and In Vivo Testing of an Electrocatalytic Glucose Sensor, *Electrocatalytic Glucose Sensor*.

Fisher, et al., Experience with an Implantable Glucose Sensor as a Prerequisite of an Artificial Beta Cell, *Biomed Biochim Acta*, vol. 43, 1984.

Lerner, H., et al., Measurement of Glucose Concentration in the Presence of Coreactants with a Platinum Electrode, *Diabetes Care*, vol. 5, No. 3 May–Jun. 1982.

Kondo, et al., Trial of new Vessel Access Type Glucose Sensor for Implantable Artificial Pancreas In Vivo, *Trans Am Soc Artif Intern Organ*, vol. 27, 1981.

Gilligan, B., J. MS, DVM, et al., Evaluation of a Subcutaneous Glucose Sensor out to Three Months in a Dog Model, *Diabetes Care*, vol. 17, No. 8, Aug. 1994.

Velho, G. et al., In vitro and In Vivo Stability of Electrode Potentials in Needle–Type Glucose Sensors, *Diabetes*, vol. 38, Feb. 1989.

Fischer, U., et al., Wick Technique: Reference Method for Implanted Glucose Sensors, *Artificial Organs*, vol. 13, No. 15, 1989.

Hashiguchi, Y., M.D., et al., Development of a Miniaturized Glucose Monitoring System by Combining a Needle–Type Glucose Sensor With Microdialysis Sampling Method, *Diabetes Care*, vol. 17, No. 5, May 1994.

Preidel, W., et al., In Vivo Experiment with the Electrocatytic Glucose Sensor in Sheep, *Biosensors & Bioelectronics*, vol. 8 pp. 299–306, 1993.

Moussy, F., et al., Performance of Subcutaneously Implanted Needle–Type Glucose Sensors Employing a Novel Trilayer Coating, *Analytical Chemistry*, vol. 65, pp. 2072–2077, 1993.

Shichiri, M., et al., In Vivo Characteristics of Needle–Type Glucose Sensor–Measurement of Subcutaneous Glucose Concentrations in Human Volunteers. (no date available).

Poitout, V. et al., A Glucose Monitoring System for on Line Estimation in Man of Blood Glucose Concentration Using a Miniaturized Glucose Sensor Implanted in the Subcutaneous Tissue and a Wearable Control Unit, *Diabetologia*, vol. 36, pp 658–663, 1993.

Koudelka, M., et al., In Vivo Behavior of Hypodermically Implanted Microfabricated Glucose Sensors, *Biosensors & Bioelectronics*, vol. 6, pp 31–36, 1991.

Sternberg, R., et al., Study and Development of Multilayer Needle–Type Enzyme based Glucose Microsensors, *Biosensors*, vol. 4, pp.27–40, 1988.

Shichiri, M. et al., Wearable Artificial Endocrine Pancras with Needle–Type Glucose Sensor, *The Lancet*, Nov. 20, 1982.

Shaw, G.W., et al., *In Vito* Testing of a Simply constructed, Highly Stable Glucose Sensor Suitable for Implantation in diabetic Patients, *Biosensors & Bioelectronics*, vol. 6 pp. 401–406, 1991.

Clark, L.C. Jr., et al., Implanted Electroenzymatic Glucose, *Diabetes Care*, vol. 5, No. 3, May–Jun. 1982.

Pickup, J., et al., Implantable Glucose Sensors: Choosing the Appropriate Sensing Strategy, *Biosensorss*, vol. 3, pp. 335–346, 1987.

Fischer, et al., Oxygen Tension at the Subcutaneous Implantation Site of Glucose Sensors, *Biochem–Biochim Acta*, vol. 48, pp. 965–971, 1989.

Kondo, T., et al., A Miniature Glucose Sensor, Implantable in the Blood Stream, *Diabetes Care*, vol. 5, No. 3, May–Jun. 1982.

Rebrin, K. et al., Subcutaneous Glucose Monitoring by Means of Electrochemical Sensors: Fiction or Reality?. *Journal of Biomedical Engineering*, vol. 14, Jan. 1992.

McKean, B., et al., A Telemetry–Instrumentation System for Chronically Implanted Glucose and Oxygen Sensor, *IEEE Transactions of Biomedical Engineering*, vol. 35, No. 7, Jul. 1988.

Claremont, D.J., et al., Subcutaneous Implantation of a Ferrocene–Mediated glucose sensor in Pigs, Diabetologia, vol. 29, pp. 817–821, 1986.

C. Meyerhoff, et al., Use of the Microdialysis Technique in the Monitoring of Subcutaneous Tissue Glucose Concentration, *The International Journal of Artificial Organs*, vol. 16, No. 5 pp. 268–275, 1993.

$O_2 \ DELIVERY = C.O. \times Hb \times Sa \ O_2 \times 1.39 + Pa \ O_2 \times 0.0031$

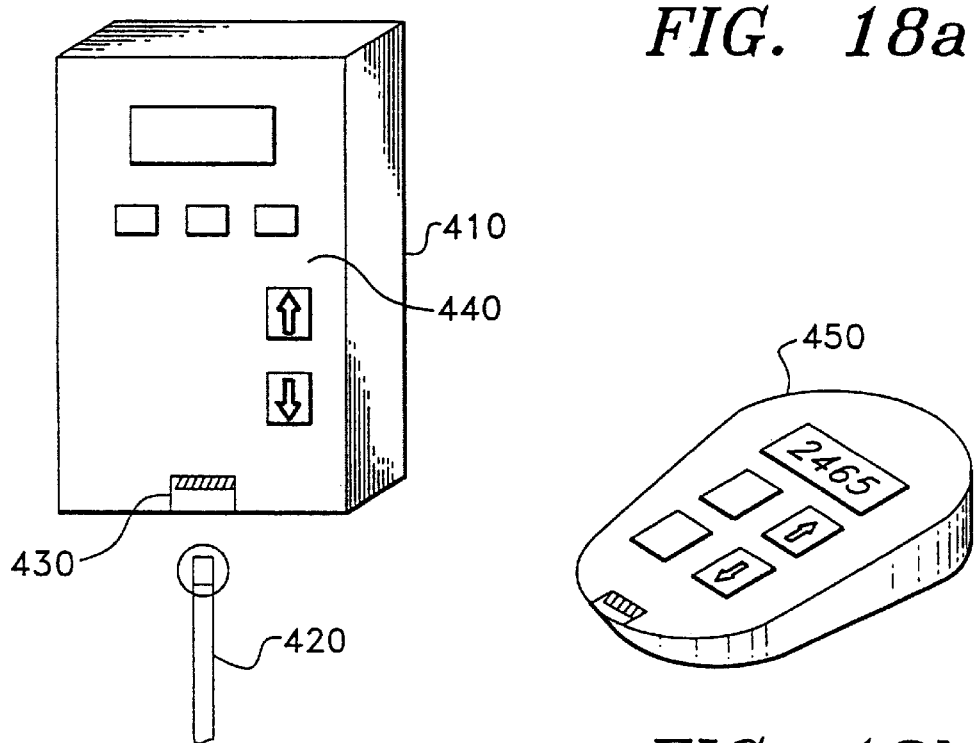
*FIG. 18a*
*FIG. 18b*
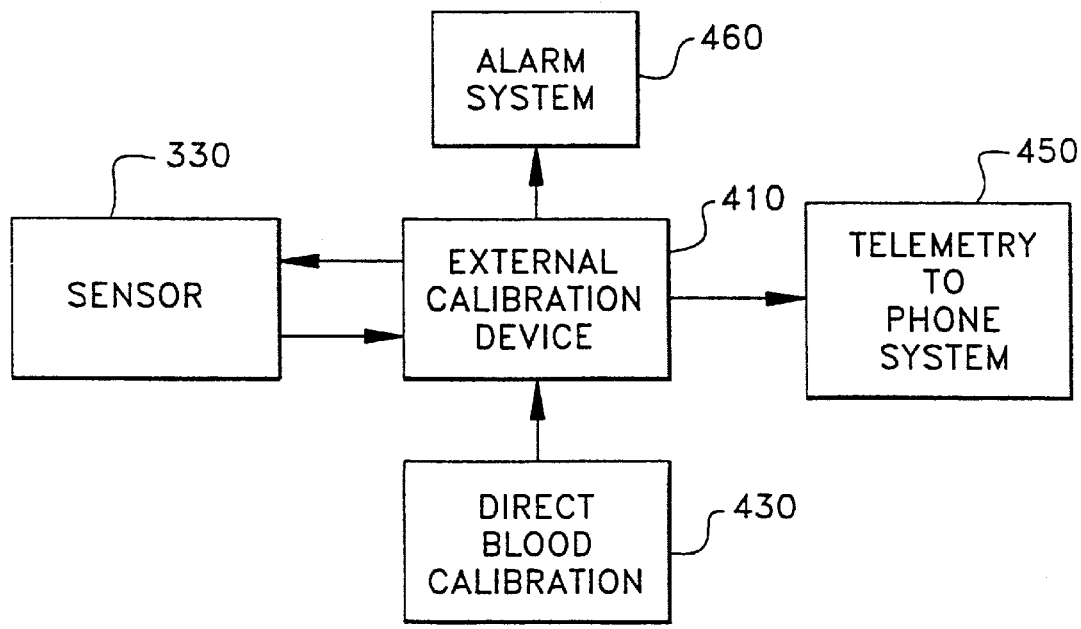
*FIG. 18c*

IMPLANTABLE SENSOR AND SYSTEM FOR MEASUREMENT AND CONTROL OF BLOOD CONSTITUENT LEVELS

CROSS-REFERENCE TO RELATED APPLICATIONS

This application is a continuation-in-part of U.S. application Ser. No. 08/500,388 filed Jul. 6, 1995, entitled "IMPLANTABLE SENSOR AND SYSTEM FOR MEASUREMENT AND CONTROL OF BLOOD CONSTITUENT LEVEL", now U.S. Pat. No. 5,995,860.

FIELD OF THE INVENTION

The present invention relates to medical devices for sensing the level of a constituent in a body fluid such as blood, including but not limited to blood glucose, oxygen, antibiotics, enzymes, hormones, tumor markers, fatty acids, and amino acid levels. The present invention also relates to a system for control, monitoring and reporting blood constituent levels in response to sensed levels and to provide continuous monitoring and control of blood constituent levels to permit aggressive therapy and concomitant clinical benefit of such therapy.

BACKGROUND OF THE INVENTION

Metabolic processes in living organisms proceed according to an exact administration of chemical compounds that are manufactured and released throughout the organism. These chemical compounds control the function as well as the condition of vital organs, tissues and processes that sustain or exist within the organism. In many instances these chemical compounds can be found in the organisms fluids including blood as in the case of mammals. These chemical compounds in the blood are generically referred to as blood constituents.

Blood Constituents

Glucose

A blood constituent such as Glucose is an important nutrient and indicator for human organisms. During periods of moderate to heavy exercise, the muscles utilize large amounts of glucose to release energy. In addition, large amounts of glucose are taken up by muscle cells in the few hours after a meal. This glucose is stored in the form of muscle glycogen, and can later be used by the muscles for short periods of extreme use and to provide spurts of energy for a few minutes at a time. Moreover, glucose is an essential nutrient for brain and spinal cord function. Glucose is the only nutrient that can normally be utilized by the brain, retina, and germinal epithelium of the gonads in sufficient quantity to supply those organs with their required energy. Brain tissue has an obligate requirement for a steady supply of blood glucose. When blood glucose levels fall below 50 mg/dl, memory loss, agitation, confusion, irritability, sweating, tachycardia, and hypertension commonly occur. Brain failure occurs when blood glucose levels fall below 30 mg/dl, and is associated with coma, hypoventilation, and vascular instability. Death may occur. Therefore, it is important to maintain the blood glucose concentration at a high enough level to provide this necessary nutrition.

At the same time, however, it is also important that the blood glucose concentration not rise too high. Glucose exerts a large osmotic pressure in the extracellular fluid. If glucose concentration rises to excessive levels, this can draw water out of the cells and cause considerable cellular dehydration. Blood sugars above 200 mg/dl often exceed renal threshold producing an osmotic diuresis by the kidneys, which can deplete the body of fluids and electrolytes.

The steady supply of blood glucose is tightly controlled by the pancreas and the liver. Following a meal, gastric digestion and intestinal absorption provide an increasing amount of carbohydrates, free fatty acids, and amino acids into the portal venous blood. Sixty percent of the glucose absorbed after a meal is immediately stored in the liver in the form of glycogen. Between meals, when the glucose concentration begins to fall, liver glycogen is dephosphorolated, allowing large quantities of glucose to diffuse out of the liver cells and into the blood stream. The liver, a large organ, can store six percent of its mass as glycogen. In contrast, muscle tissue can store only two percent of its mass as glycogen, barely enough to be used by the muscle as its own energy reserve.

Normally, blood glucose concentration is regulated by two hormones, insulin and glucagon, secreted by the pancreas. Insulin is released in a bimodal fashion from the pancreas in direct response to a rise in blood glucose level and, to a lesser extent, to a rise in the blood level of free fatty acids and amino acids. Insulin promotes transport of these nutrients into the cells to be utilized for energy, to be stored as glycogen or triglycerides, or to be synthesized into more complex compounds such as proteins.

Some individuals develop diabetes mellitus, and do not secrete insulin in sufficient quantities to properly regulate blood glucose. Lack of insulin inhibits the cell membrane transport of nutrients such as glucose, fatty acids, and amino acids into the cells, forcing the cells to use other compounds for energy and cell growth. Diabetics exhibit a decreased utilization of those nutrients by the cells, resulting in a marked increase in blood glucose concentration, an increase in triglyceride mobilization from the adipose tissue resulting in a marked increase in blood fatty acid and cholesterol concentrations, and a marked loss of protein on a cellular level. Many of the severe end-organ complications which result from diabetes are due to the cellular wasting which occurs secondary to abnormal amino acid uptake and protein wasting. Abnormal fatty acid metabolism results in elevated levels of blood concentrations of low-density lipoprotein (LDL), cholesterol, and free fatty acids, all leading to accelerated atherosclerosis and obstructive vascular disease. Those with diabetes are also prone to ketosis, and develop dehydration, acidosis, and electrolyte imbalance under stress. In some forms of the disease, insulin injections may be required, and other long-term complications such as retinopathy, blindness and kidney disease commonly occur.

The pancreas also secretes glucagon, a hormone which has cellular functions that are diametrically opposed to those of insulin. Glucagon stimulates the liver to release large amounts of glucose from glycogen when the blood glucose concentration falls below 90 mg/dl. This system of insulin inhibition and glycogen release prevents glucose concentrations from falling dangerously low.

In short, glucose is regulated within a narrow range between 80 and 90 mg/dl during fasting, with a rise toward 140 mg/dl following a high carbohydrate meal. The liver functions as a reservoir and buffer, so that glucose is available to the brain during meals and during periods of prolonged fast.

Type I diabetics have an absolute deficiency in insulin synthesis by the beta cells of the pancreas, and have the most severe clinical course if not aggressively managed with nutrition and insulin therapy. These individuals are ketosis prone and may develop a severe metabolic acidosis. Wide swings in blood glucose commonly occur with a high incidence of symptomatic hypoglycemia following insulin therapy. End organ dysfunction is common due to accelerated atherosclerosis, cellular protein wasting, and small vessel disease.

Type II diabetics release insulin from the pancreas in a blunted fashion following the intake of food. Blood insulin levels do not rise sufficiently to prevent hyperglycemia. However, in some forms of the disease, insulin levels may be elevated. In addition, peripheral tissues of type II diabetics may possess a smaller number of membrane tissue receptors and possibly a down regulation of those receptors. Ketoacidosis is uncommon. However, hyperglycemia and hyperosmolar conditions may occur, leading to coma and death. Insulin therapy may or may not be required to maintain normal glycemia levels. Other therapies include weight loss, diet, and oral hypoglycemic agents which stimulate the pancreas to release larger quantities of insulin.

There is no doubt that long term tight glucose control is able to significantly reduce the incidence of end organ complications. Control of blood glucose concentration in diabetic individuals by Q.I.D. insulin injections has, of course, been done for many years. This type of treatment does have a number of serious drawbacks, however. One or more needle sticks of the finger must be performed on a daily basis to obtain blood for glucose assay. Many patients suffer anxiety and discomfort when subjected to finger pricking. After the blood sample is obtained, the sample must be exposed to a surface coated with chemical agents and enzymes that produce a color change corresponding to glucose concentration. The patient or medical practitioner performing the assay must interpret the color change accurately, and inject a dose of insulin based on the glucose level. Some patients use a hand held glucometer to measure glucose concentrations in their blood. Many individuals experience anxiety and discomfort when facing injections, and resist them. Some individuals may have no one to administer the required injections, but have difficulty injecting themselves. Dosage can also be problematic. Color change can be misinterpreted, and it is not unusual for patients to miss an injection, or to be off schedule. In addition, patients even have difficulties when using glucometers. Syringes, which these days tend to be disposable, contribute to the growing problem of hazardous medical waste.

Some of these problems have been partially dealt with in the past, but none of the past attempts at dealing with these problems has been entirely satisfactory. Non-invasive optical techniques for measuring blood glucose have been developed, but these techniques do not solve the problems associated with administering insulin injections where required. Non-invasive optical techniques for measuring blood glucose are prone to error because the interface between the sensor and the tissue changes constantly with manipulation and contact pressure. Skin and extremity blood flow also varies considerably with cardiac output, body temperature and level of activity. These non-invasive optical techniques typically use a source of infrared (IR) radiation and a detector to measure absorption, reflection, or some other parameter to derive information about blood glucose levels. The effective optical distance from the IR source and the detector changes with subcutaneous body fat and the variability in placing the sensor from day to day. In addition, non-invasive IR sensors measure blood glucose in a non-continuous manner, and are thereby limited to functioning as a glucose measuring device and not as a therapeutic device for the treatment of diabetes.

Implantable pumps for administering insulin as well as other chemical compounds are known. It has even been proposed to automatically measure blood glucose and administer insulin as may be required using an implantable sensor and insulin pump system. The latter systems are know to incorporate sensors to perform chemical analysis of blood samples which require the introduction of chemical reagents into the patient's body. Typically, these reagents periodically need to be replenished, which imposes the requirement of access below the surface of the skin through which fresh reagents must be injected from time to time. No matter what sensor is used, insulin still must be injected approximately every 6 weeks into the pump reservoir by placing a thin needle through the skin. Moreover, commercially available implantable pumps have FDA approval only for the infusion of chemotherapy and Baclofen for the treatment of spastic leg disorders. Pumps implanted for the infusion of insulin have been successfully tested in humans, however, there is no clinical benefit to implantations without a sensor for closed-loop control.

Oxygen

Cells require a continuous supply of oxygen and nutrients for basic metabolism. Oxygen must be efficiently absorbed through the lungs and combined with hemoglobin in the blood for proper transport to the tissues. Oxygen delivery depends upon the pumping action of the heart (blood flow per minute) and the content of oxygen bound to hemoglobin and dissolved within the plasma.

Once in the tissues, oxygen is released from the hemoglobin molecule and diffuses through the interstitial fluid and into each cell. The workhorse of any mammalian cell is the mitochondria. A series of surface bound enzymes within the mitochondria transfer electrons generated during the metabolism of glucose called the Krebs' Cycle. Oxygen acts as the final electron acceptor generating ATP, NADH, heat, and carbon dioxide as a waste product. High energy phosphate compounds such as ATP and NADH are generated to provide energy for most cellular metabolic processes. Examples of processes requiring ATP for energy include: maintaining ionic gradients, active membrane transport, intracellular synthesis, and cell reproduction. Highly metabolic tissues such as brain and heart muscle tolerate an inadequate delivery of oxygen and other nutrients poorly. Conditions that produce a low blood flow state include cardiac pump failure, hemorrhage, dehydration, and sepsis. The tissues attempt to compensate for this low blood flow state by extracting a greater portion of the delivered nutrients.

When oxygen delivery is insufficient to supply the aerobic needs for ATP production, alternative metabolic pathways will dominate causing lactic acid to accumulate. Anaerobic metabolism produces an insufficient supply of high energy compounds and cellular functions quickly deteriorate. Ionic gradients are lost and repair mechanisms cease to function. Persistent low flow states lead to ischemic damage to various end-organs including the kidneys, brain, and liver. Hypoxemia and metabolic acidosis proceeds organ failure followed by death of the mammal.

Large multicellular organisms require a distribution system for the delivery of oxygen and nutrients. The heart, blood vessels, and hemoglobin molecules efficiently transport oxygen and other nutrients to the peripheral tissues such that every cell is within diffusion distance of a nutrient capillary. Typically, the heart provides pulsatile blood flow (cardiac output) exceeding 5.0 liters per minute. During periods of increased metabolic activity such as exercise, infection, or following surgery, the cardiovascular system is required to increase the cardiac output several fold to meet the increased oxygen requirements. Many disease states compromise the cardiovascular system such that an inadequate supply of oxygen and nutrients reach the tissues. Chronic heart failure due to hypertension, ischemic heart disease, valve disease, or alcohol is the most common cause of death in the U.S.

Fatigue, shortness of breath, and poor exercise tolerance are common as the failing heart is unable to pump sufficient quantities of blood to satisfy the metabolic needs of the tissues. In addition, cardiac arrhythmia may further compromising forward blood flow. To solve some of these problems, physicians are can only intervene with medications and supplemental oxygen improving oxygenation and blood flow to the vital organs.

Devices and Implantable Sensors for Detection of Blood Constituents

Devices for the detection of blood glucose incorporate an implantable sensor using a semipermeable membrane and an enzyme coated surface and an oxygen electrode have been studied for the continuous measurement of blood glucose. This sensor has significant drift and quickly fails due to host reaction and contamination of the membrane and enzyme surface. Needle-type amperometric glucose sensors implanted within the subcutaneous tissues and having an enzyme coated surface and an electrical output to an external processor are known, but loss of sensitivity and sensor drift occur upon implantation. This type of sensor, which is in the form of a thin wire, must be inserted through a hollow needle into the subcutaneous tissue and must be changed every three to four days due to enzyme depletion and membrane contamination. In addition, glucose concentration within the subcutaneous tissues lags 20 minutes behind blood glucose and varies between 70–80% of blood values.

Devices for the detection of blood oxygen such as a pulse oximeter are well known. The oximeter measures blood oxygen by measuring the amount of light absorbed by hemoglobin at two different frequencies. It was observed that oxygenated hemoglobin absorbs light differently from that of reduced hemoglobin at two certain frequencies. For example, at 660 nanometers, reduced hemoglobin is known to absorb as much as ten times the amount of light as oxygenated hemoglobin, whereas oxygenated hemoglobin absorbs a much greater amount of light at the infrared wavelength of 940 nanometers. In addition, the absorbed light has a pulsatile sinusoidal component caused by pulsing volumes of arterial blood from the heart.

The typical pulse oximeter has two light emitting diodes (LEDs) and a detecting sensor arranged in a noninvasive manner to allow emitted light to pass through body tissue for detection by the sensor. As the light passes through the body tissue it is partially absorbed as described above and then detected to produce an estimate of blood oxygen in the human body.

Pulse oximeters have been developed for continuous measurement of in-vivo human blood oxygen saturation by transilluminating tissue noninvasively. However, these devices have several disadvantages. Because the pulse oximeter is external to the body and noninvasive, it can only measure red and infrared light transmitted through blood in human tissue, typically the ear or finger. As a consequence, several inaccuracies are introduced into the measurement of oxygenated hemoglobin by the absorption and dispersion of light through intervening tissues such as skin, soft tissue, bone, venous blood and arterial blood. In addition, the sensors of a pulse oximeter are susceptible to interference from ambient light, low perfusion, and body motion. Pulse oximetry is known in the art and further described in Kevin K. Tremper and Steven J. Barker, "Pulse Oximetry", *Anesthesiology*, Vol 70, pp 70–108 1989 which is incorporated herein by reference.

Therefore there is a need to control levels of blood constituents, such as glucose concentration, oxygen, fatty acid concentration, and amino acid concentration without requiring blood sampling, chemical test reagents or reagent injections, and with continuous monitoring of levels of blood constituents. The present invention meets that need by providing a sensor which is fully implantable and can be used In-vivo, can be used continuously and over the long term, and which is reliable and safe.

The present invention provides the ability to achieve close, continuous monitoring and control of blood constituents such as, but not limited to, glucose and oxygen, as well as tumor markers, antibiotics, enzymes, hormones, fatty acids, and amino acid levels, thereby providing a clinical and therapeutic breakthrough.

SUMMARY OF THE INVENTION

The present invention is an implantable sensor and system capable of measuring, controlling, monitoring, and reporting blood constituent levels. The invention includes an implantable device for sensing In-vivo the level of at least one blood constituent in mammalian vascular tissue. The internal device includes a communication system and a calibration system.

In one aspect of the invention, the implantable device comprises at least one source of radiation from infrared through visible light, arranged to direct the radiation at the tissue. The radiation is affected by interaction with the tissue and detected by a plurality of detectors. The detectors are located with respect to the tissue to receive radiation affected by said tissue. The detectors each have a filter transparent to a discrete narrow band of radiation. Each detector provides an output signal representative of detected radiation in said narrow band.

In another aspect of the invention, the implantable device comprises at least two sources of radiation from infrared through visible light, arranged to direct the radiation at the tissue. The radiation is affected by interaction with the tissue and detected by at least one detector. The detectors being located with respect to the tissue to receive radiation affected by said tissue. Each source is adapted to emit radiation in a selected number of discrete bandwidths and each detector is adapted to detect the radiation being emitted in the discrete bandwidth. Each detector provides an output signal representative of detected radiation in said discrete bandwidth.

In another of its aspects, the present invention includes a device for both measuring and controlling the level of a blood constituent in a mammal, and comprises an implantable infrared source and sensor module for directing infrared radiation through vascular tissue such as, but not limited to, an artery, a vein, a vascular membrane, or vascular tissue. The sensor module senses the infrared radiation after it has passed through the tissue and generates an output signal representative of the sensed infrared radiation. A processor module, responsive to the output signal from the infrared source and sensor module, performs spectral analysis of the output signal and derives therefrom a control signal representative of the level of the blood constituent. The processor module or another device in communication with the processor module is used to control, monitor, and report the level of the blood constituent.

In one aspect of the invention, an insulin pump is used to control the level of glucose by dispensing doses of insulin in response to the control signal. In another aspect of the invention, an implanted cardiac pacemaker as well as an internal cardiac defibrillator (ICD) is used to control the level of oxygenated hemoglobin in the blood in response to the control signal. In yet another aspect of the invention, an implanted dispensing device is used to control the level and administration of medications such as, but not limited to, cardiac drugs, antibiotics, or chemotherapies in response to the control signal. In still another aspect of the invention, the level of tumor markers is monitored and reported to other devices in response to the control signal. In all aspects of the invention, the system is capable of monitoring and reporting all blood constituents that are sensed and measured.

In another aspect of the invention, an implantable oxygenation, hemoglobin, and perfusion sensor is provided to obtain frequent objective data on patients with chronic illnesses such as heart failure and respiratory failure. Patients would be monitored for changes in hemoglobin oxygen saturation (pulse oximeter), hemoglobin concentration (infrared measurement), and changes in tissue perfusion (analysis of the photoplethsmograph waveform) for the purpose of detecting cardiovascular decompensation early so that the physician can manage the problem as an outpatient. Visits to the emergency room and admissions to the ICU would significantly diminish. Data from the sensors will be stored within a memory chip and Physicians would be notified automatically if data changed significantly from data established for an individual patient's background.

Typically, cardiovascular patients are not alerted to significant cardiovascular decompensation until overt symptoms have occurred resulting in the need for acute care in an ICU following admission through an emergency room. With this implantable sensor of the present invention, physicians will be able to detect early cardiovascular decompensation and institute corrective therapy as required.

Data stored in a memory by the invention can provide the patient or clinician, either directly of remotely, with the natural history of the disease process. The physician will be able to administer medical therapy based on an objective presentation of data and conclude from the data and immediately acquire information on the effects of the therapy applied. The invention provides the major determinants of oxygen delivery to the tissues which are measured by the sensor.

For example, after a patient is stabilized following a myocardial infarction and the onset of heart failure and pulmonary edema, a sensor would be implanted under local anesthesia. The sensor would immediately provide and collect data directly and communicate data to an extracorporeal device for remote monitoring of the patient for changes in oxygenation, perfusion, hemoglobin concentration, and cardiac arrhythmia. Once discharged from the hospital, the sensor would continue to monitor the patient and provide data extracorporeally for significant changes in oxygenation, perfusion, hemoglobin concentration, and cardiac arrhythmia. Depending on the condition of the patient, data would be stored in a memory or reported directly to the patient or medical personnel for interpretation as required. Therefore, the present invention can facilitate the administration of medications, appropriately according to objective measured data thereby improving cardiac contractility and improved tissue blood flow in advance of an acute event.

In another aspect of the invention, the implantable device comprises at least one radiation source consisting of at least two discrete spectral bands lying somewhere within the infrared through visible spectrum, arranged to direct the radiation at the tissue. The radiation is affected by interation with the tissue and detected by at least one detector. The different spectral bands in each source are substantially collinear and interact with substantially identical tissue. The detectors being located with respect to the tissue to receive radiation from source affected by said tissue.

Discrimination amongst different spectral bands is provided by each spectral band having a unique temporal or frequency modulation. Each detector provides an output signal representative of detected radiation from said source. A communication means is provided to relay the output signal from detector to processor. A processor is used to determine level of blood constituent in blood.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 18a is an illustration of an extracorporeal calibration and communication module unit for use in connection with implantable blood constituent sensor modules according to the invention.

FIG. 18b is an illustration of a extracorporeal calibration handheld unit for use in connection with implantable blood constituent sensor modules according to the invention.

FIG. 18c is a functional block diagram showing the operation of an implantable device according to the invention in communication with the extracorporeal calibration and communication module shown in FIG. 18a.

DESCRIPTION OF THE INVENTION

Figure 1:
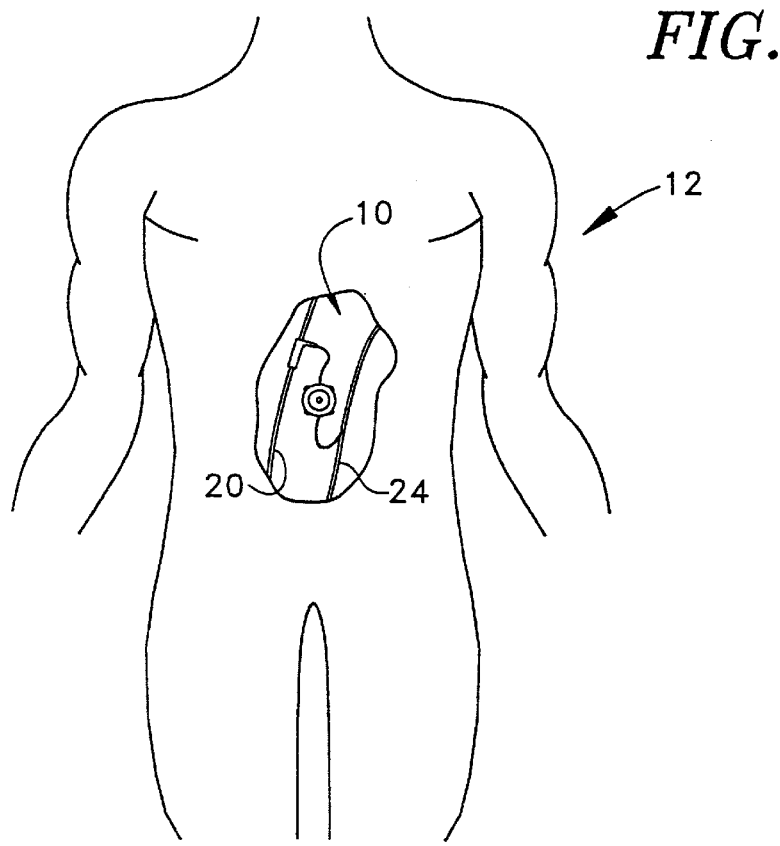
FIG. 1 illustrates an implantable glucose sensor according to one embodiment of the invention as it might be implanted in a human patient, shown in conjunction with an implantable insulin pump, with the sensor array arranged to monitor blood flow through a blood vessel.

Referring now to the drawings, wherein like numerals indicate like elements, there is shown in FIG. 1 a representation of an implantable blood constituent monitoring and control system 10.

Glucose Monitoring and Control System

FIG. 1 shows a blood glucose monitoring and control system 10 comprising a sensor and an insulin pump, as it might be surgically implanted in a patient 12. It should be understood that FIG. 1 is not intended to be anatomically accurate in every detail; rather, it is intended to represent generally how the system 10 would be implanted. Moreover, it should also be understood that, while for convenience the present invention is illustrated and described in reference to monitoring and control of blood glucose, the invention is not so limited, and encompasses the monitoring and control of other blood constituents such as, by way of example and not by way of limitation, fatty acid or amino acid concentration. Several preferred embodiments of the invention are presented below.

Figure 2:
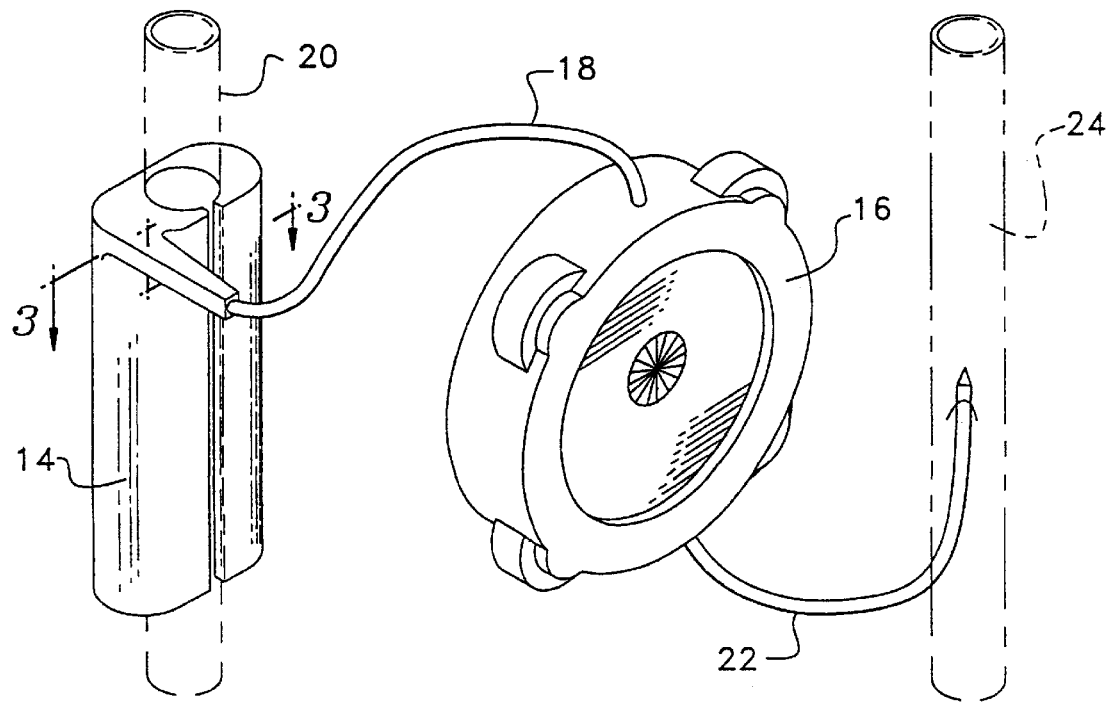
FIG. 2 is an enlarged view of the sensor of FIG. 1, showing the sensor in conjunction with an implantable insulin pump and processor module containing associated processing and control electronics.

As best seen in FIG. 2, system 10 comprises a sensor assembly 14 connected to a processor/pump module 16 via a signal cable 18. Sensor assembly 14, described in greater detail below, has an opening which enables it to be arranged to substantially surround a blood vessel 20. Processor/pump module 16 is illustrated as dispensing insulin via a tube 22 into a second blood vessel such as a vein 24, which may be the portal vein for direct transport to the liver. Alternatively, processor/pump module dispenses insulin via a non-thrombogenic multilumen catheter including a one-way valve, directly into the peritoneal space adjacent the hilum of the liver. Insulin will be rapidly absorbed into the portal venous system and transported to the liver. While the processor/pump module 16 is illustrated as implanted within a patient's body, the pump portion of processor/pump module 16 may also be an external device, worn or otherwise carried by the patient, without departing from the present invention. Where an external pump is used, insulin may be delivered percutaneously into an infusaport implanted under the patient's skin for final transport to the peritoneal cavity or portal vein. Alternatively, insulin may also be delivered by an external device with a needle placed chronically within the patient's subcutaneous tissues. Moreover, when an external pump is used, the processor portion of processor/pump module 16 requires a data telemetry portion in order to telemeter command signals to the external pump. Insulin reservoirs and pumps, telemetry devices, and infusaports are all known per se, and therefore need not be described here in any great detail.

Processor/pump module 16 contains a conventional insulin reservoir and pump. In addition to an insulin reservoir and pump, processor/pump module 16 contains an electronic microprocessor and associated electronic circuitry for generating signals to and processing signals from sensor assembly 14 and for generating control signals to the insulin pump itself. Processor/pump module 16 further includes a long-life battery to power the electronic circuitry, the sensor assembly 14 and the insulin pump.

Blood Constituent Sensor

Figure 3:
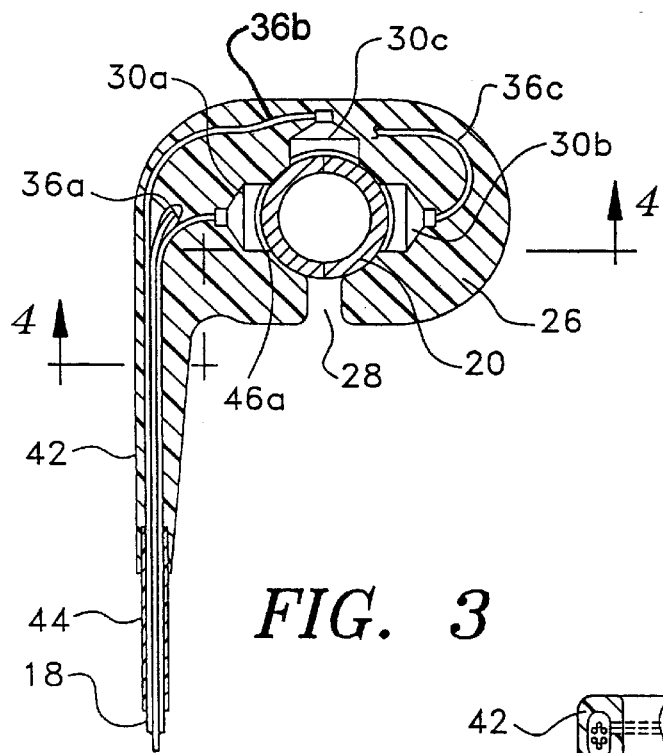
FIG. 3 is a transverse sectional view through the sensor shown in FIG. 2, taken along the lines 3—3 in FIG. 2, showing the distribution of individual photocells.
Figure 4:
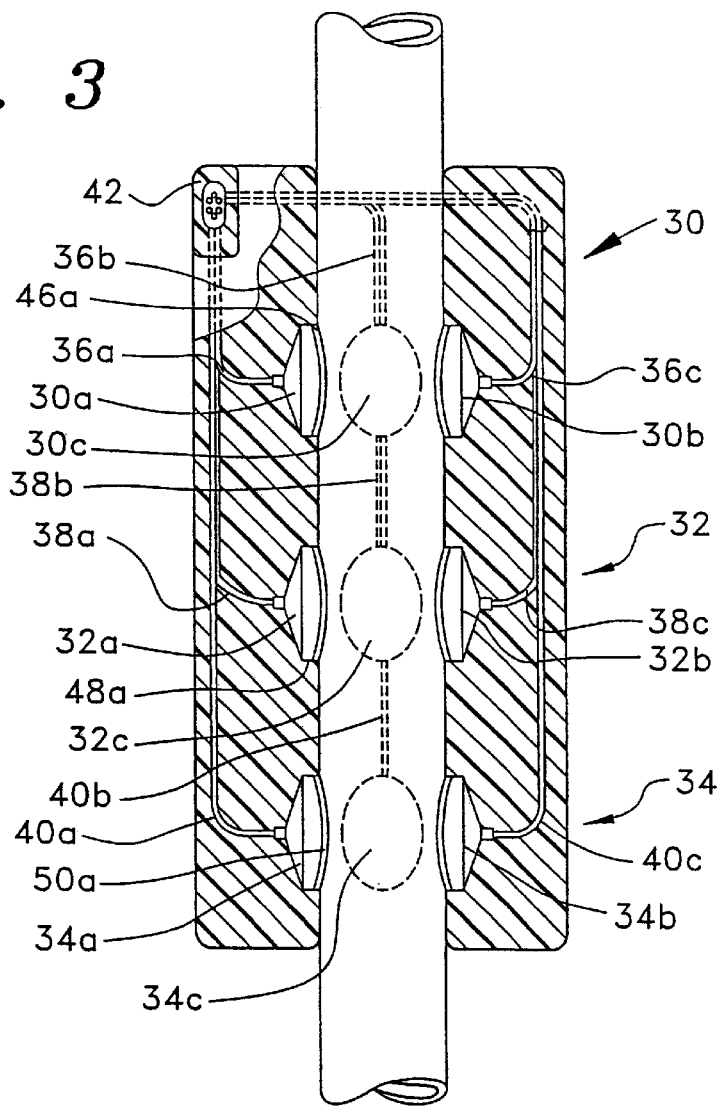
FIG. 4 is a longitudinal sectional view through the sensor, taken along the lines 4—4 in FIG. 3.
Figure 5:
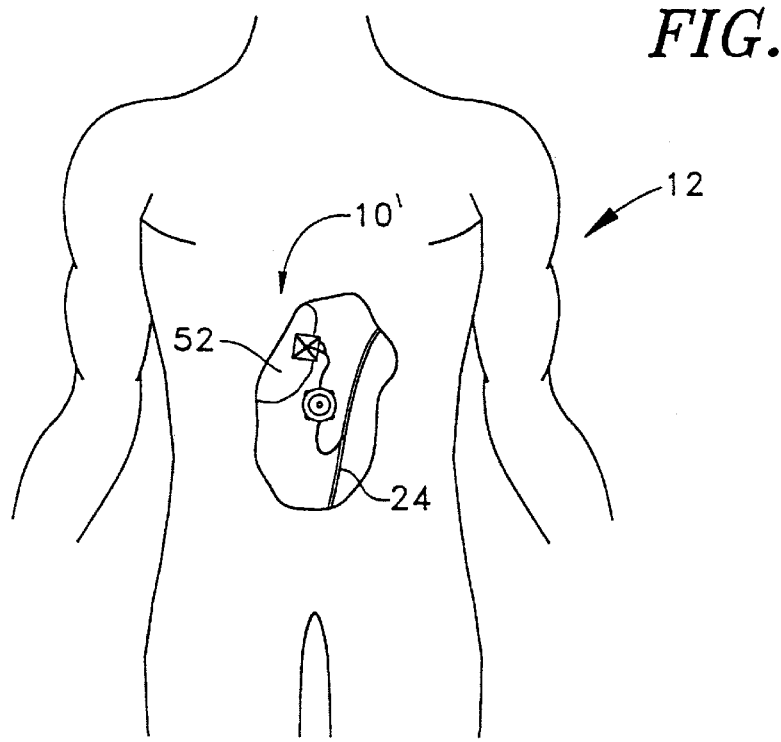
FIG. 5 illustrates an implantable glucose sensor according to an alternate embodiment of the invention as it might be implanted in a human patient, with a sensor array arranged to monitor blood flow through a vascular membrane such as parietal peritoneum.

Sensor assembly 14 is illustrated in greater detail in FIGS. 3 and 4. Sensor assembly 14 has a body portion 26 which is generally C-shaped in transverse cross-section. Thus, body portion 26 has a longitudinal channel which runs through body portion 26, and a longitudinal gap 28 which communicates with the longitudinal channel. Body portion 26 is preferably fabricated from a semi-rigid material such as titanium or epoxy, which is easily worked and biocompatible for long-term implantation. The shape and semi-rigid material of sensor assembly 14 enables it to be placed closely around vessel 20 and place optical sources and individual optical detectors in optimum position with respect to vessel 20. The distance between the optical sources and the optical detectors can thus be made small and as close to constant as possible, for optimum signal acquisition.

In the embodiment of sensor 14 illustrated in FIGS. 3 and 4, the optical sources and optical detectors may be infrared (IR) sources and IR detectors, although radiation from infrared through the visible spectrum may be employed without departing from the invention. In the figures, individual IR sources and individual IR detectors are grouped together in three groups, or arrays, 30, 32, and 34. Each array comprises an IR source (30a, 32a, and 34a, respectively) and two IR detectors (30b, 30c; 32b, 32c; and 34b, 34c, respectively). The individual IR sources 30a, 32a, and 34a may be miniature infrared diodes located, in the illustrated embodiment, on one side of vessel 20. IR sources 30a, 32a, and 34a are driven by signals generated in the processor/pump module 16 and transmitted to IR sources 30a, 32a, and 34a via conductors 36a, 38a, and 40a, respectively. Similarly, output signals from individual detectors 30b, 30c; 32b, 32c; and 34b, 34c are transmitted to processor/pump module 16 via conductors 36b, 36c; 38b, 38c; and 40b, 40c, respectively. Conductors 36, 38, and 40 collectively are dressed together to form signal cable 18, which couples sensor array 14 to processor/pump module 16. Cable 18 exits body portion through an extension portion 42, which serves to support cable 18 and minimize the chance of breakage of conductors 36, 38, and 40 from flexing or being subjected to sharp bends. If desired, cable 18 may exit extension portion 42 through a strain relief sleeve 44, to further protect cable 18.

Each IR source 30a, 32a, and 34a has associated with it an optical filter 46a, 48a, and 50a, respectively. Each filter transmits a different discrete narrow band of radiation. In similar fashion, each detector 30b, 30c; 32b, 32c, and 34b, 34c has associated with it an optical filter 46b, 46c; 48b, 48c; and 50b, 50c, respectively. In this manner, each optical source and the detectors associated with it in a given array 30, 32, or 34 operates in only a discrete narrow band.

With this embodiment, detectors 30b, 32b, and 34b are arranged diametrically opposite IR sources 30a, 32s, and 34a, respectively, to detect light transmitted from the associated source through the blood vessel 20. The angle between the sources and the detectors is thus 180°. (These detectors could also be used to determine reflected light, since light that is not transmitted may, for purposes of the invention, be assumed to have been reflected. By determining the amount of light transmitted, and subtracting it from the amount of light emitted from the source, the amount of light reflected can be calculated.) Detectors 30c, 32c, and 34c are arranged at an angle less than 180° from the associate sources, and are located to detect IR radiation either reflected or scattered from vessel 20.

It is important to note that, although this embodiment of the invention is described using three arrays of IR sources and associated detectors, that precise configuration is not crucial to the invention. The invention may be implemented, for example, using a single IR source and multiple detectors for detecting reflected, scattered, and transmitted IR radiation. In such an embodiment, the IR source would not have a narrow band filter associated with it, but would emit broadband IR. Each detector, however, would have a narrow band filter associated with it, so that it would respond only to a preselected wavelength.

Conductors 36, collectively, 38, collectively, and 40, collectively, can be either electrical conductors or optical fibers. That is, the IR sources and the IR detectors may be located either within sensor assembly 14 itself, in which case the conductors are electrical conductors and carry electrical signals between processor/pump module 16 and sensor assembly 14, or within processor/pump module 16, in which case the conductors are optical fibers and carry infrared radiation between processor/pump module 16 and sensor assembly 14.

It will be appreciated that IR radiation generated by IR sources 30a, 32a, and 34a is directed through the walls of vessel 20, and thus the blood flowing in the vessel, to detectors 30b, 30c; 32b, 32c; and 34b, 34c located across from and at right angles to the IR sources. The IR radiation detected by the several detectors is, of course, affected by its interaction with vessel 20 and the blood flowing therethrough. Consequently, by analyzing the output signals from the several detectors, it is possible to derive information about the levels of glucose, fatty acids, and amino acids in the blood flowing through vessel 20. Preferably, although not necessarily, selected sensor/detector pairs are used for different measurement techniques. For example, pair 30a, 30b could be used to measure infrared transmittance, and pair 30a, 30c to measure infrared scattering. That is, the output signals from the several detectors can be processed differently to obtain different characteristics of the blood being measured.

In contrast to prior electro-chemical glucose sensors, sensor array 14 does need require direct contact with blood, does not need to be replenished with test reagents, and can operate indefinitely.

Alternative Blood Constituent Sensor

In another embodiment, source 30a or 32a, or 32a) may consist of multiple LEDs or multiple laser diodes, each of a different wavelength spaced identically collinear or spaced very closely so that each wavelength has substantially the identical optical path ad interacts with substantially identical tissue. The detector 30b or c, 32b or c, and 34b or c detects light from each individual wavelength from source 30a, 32a, and 32c, respectively. The processor discriminates amongst the different wavelengths by having each wavelength pulse at a different frequency or at a different time. As the processor can discriminate amongst the different wavelengths by either different frequency or temporal information, narrow wavelength filters 46a, 48a, and 50a are unnecessary in this embodiment. Multiple sources and multiple detectors provide redundancy or alternatively the ability to measure different chemical species, although in many cases a single source and detector is adequate. The operation of the sensor is otherwise the same as described in the previous embodiment.

Vascular Membrane Sensor Interface

Figure 6:
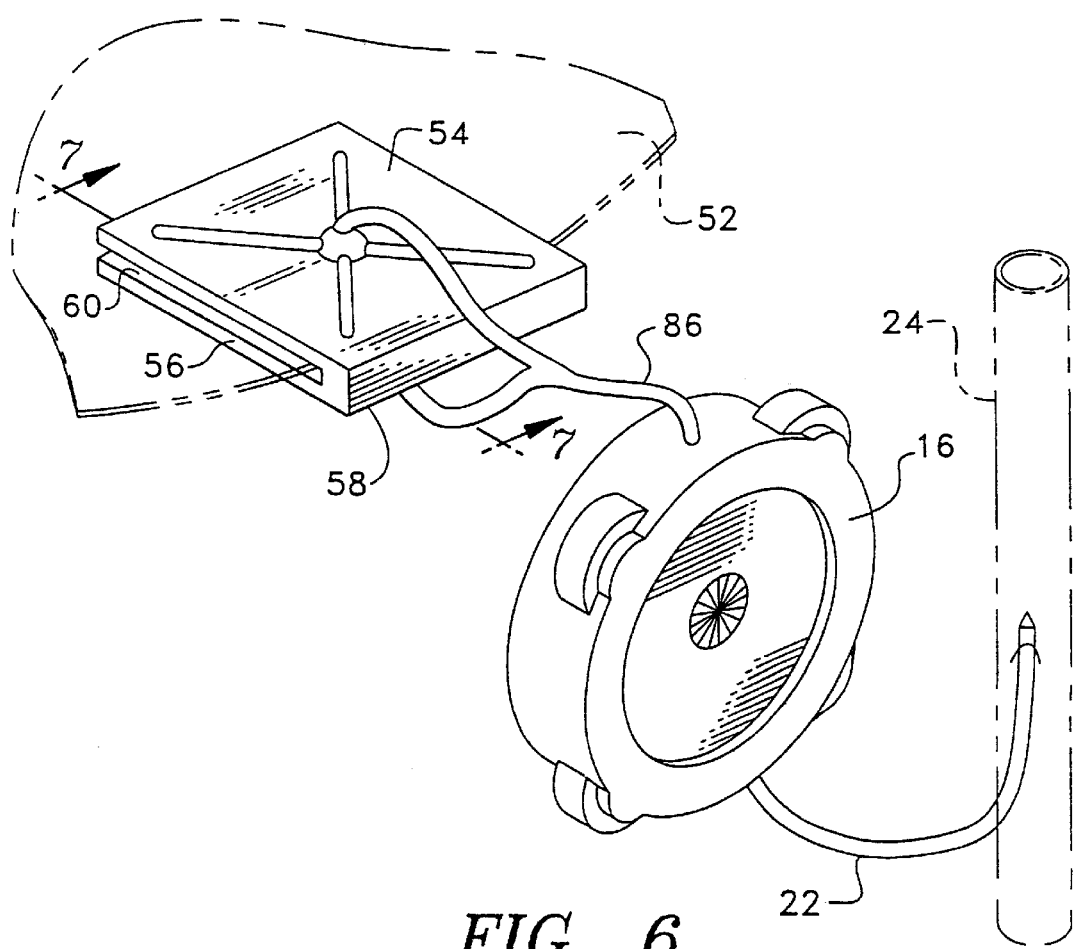
FIG. 6 is an enlarged view of the embodiment of the sensor of FIG. 5, showing the sensor in conjunction with an implantable insulin pump and processor module containing associated processing and control electronics.
Figure 7:
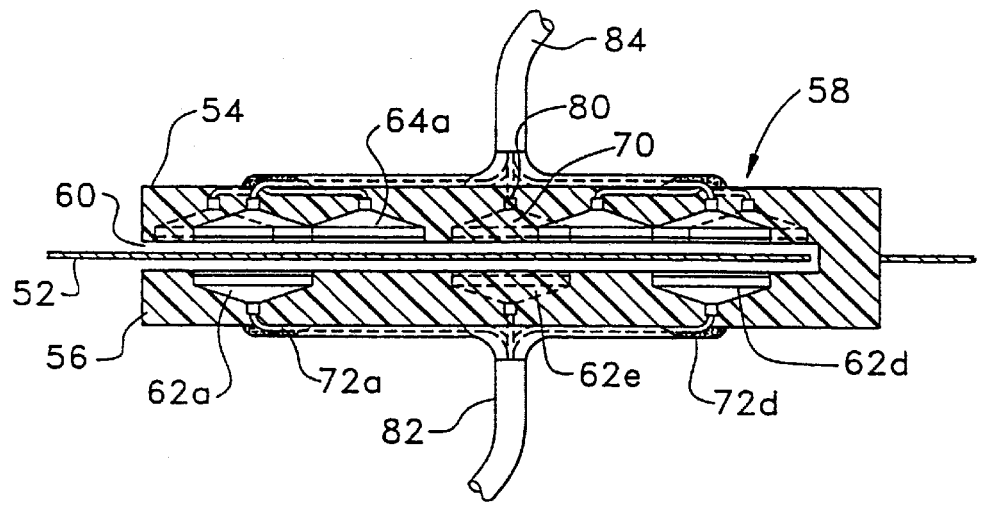
FIG. 7 is a sectional view through the sensor shown in FIG. 6, taken along the lines 7—7 in FIG. 6.
Figure 8:
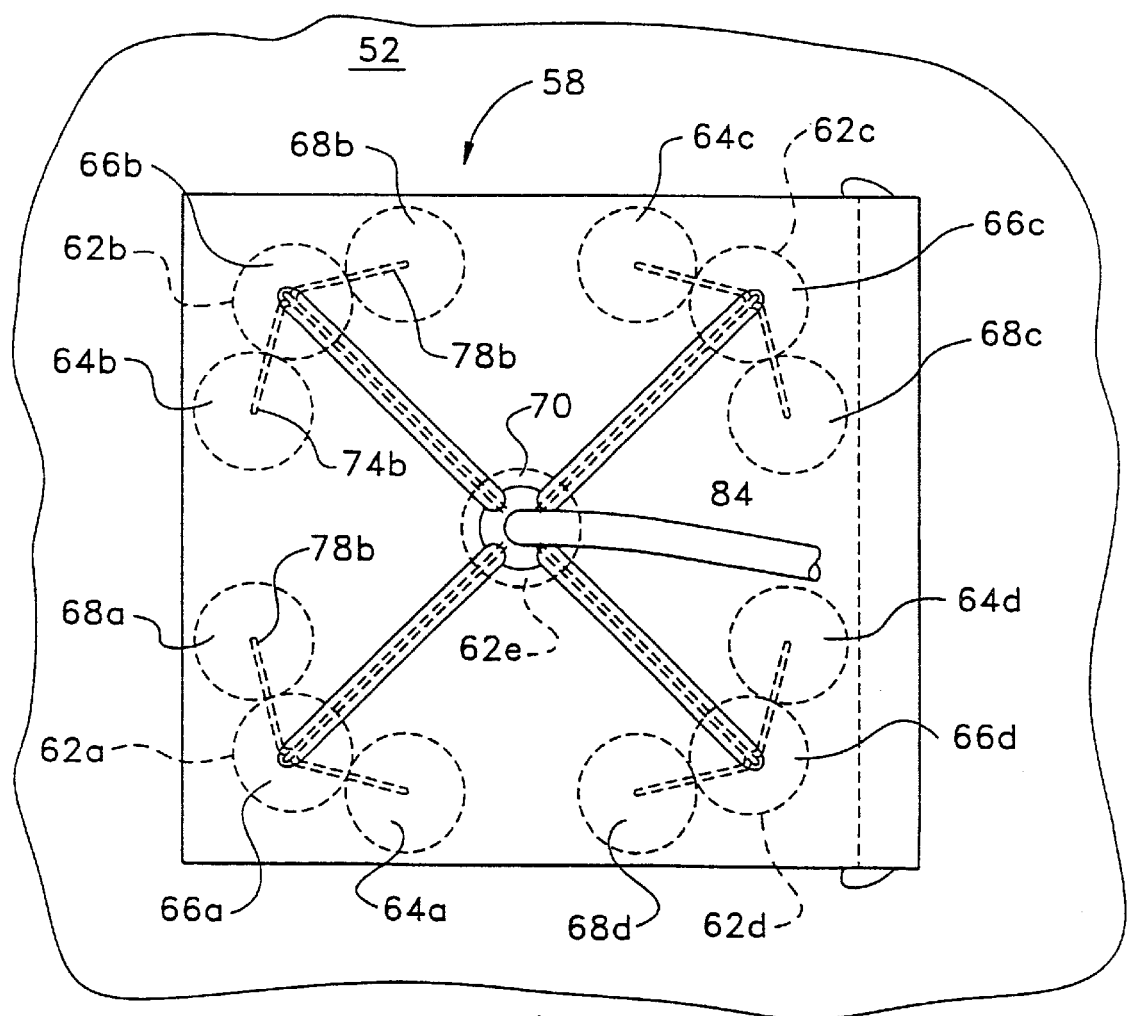
FIG. 8 is a top plan view of the sensor shown in FIG. 6, showing the distribution of individual photocells.

An alternative form of device 10' according to the present invention is illustrated in FIGS. 5 through 8. In alternative form 10', the device monitors blood flowing through a highly vascular membrane, such as a portion of the parietal peritoneum 52. The parietal peritoneum is an ideal tissue for measurement due to its high vascularity, translucency, constant temperature, and brisk blood flow. As best seen in FIGS. 6 and 7, a portion of a vascular membrane such as the parietal peritoneum 52 (shown in phantom in FIG. 6) is sandwiched between two halves 54 and 56 of an alternate form 58 of sensor assembly. Halves 54 and 56 are essentially mirror images of each other, and define a gap 60 between them, which receives the peritoneal tissue. Sensor assembly 58 is preferably molded from the same type of material as used to fabricate sensor assembly 14, as already described. The shape and semi-rigid material of sensor assembly 58 enable it to be clamped snugly around peritoneal tissue 52 and to place individual IR sources 62a though 62d and individual IR detectors 64a through 64d, 66a through 66d, 68a through 68d, and 70, in optimum position with respect to tissue 52.

One half of sensor assembly 58, such as half 56 for example, contains the individual IR sources 62a through 62e, while the other half, such as half 54, for example, contains the individual detectors 64 collectively, 66 collectively, 68 collectively, and 70. The detectors are grouped together in groups of three, for example, such as 64a, 66a, and 68a, and are located opposite a source, such as 62a. Only a single detector 70 is shown located opposite source 62e, although a group of detectors could also be located opposite source 62e.

IR sources 62, collectively, are driven by signals generated in the processor/pump module 16 and transmitted to IR sources 62a through 62e via conductors 72a through 72e, respectively. Similarly, output signals from individual detectors 64a through 64e, 66a through 66e, 68a through 68e, and 70 are transmitted to processor/pump module 16 via conductors 74a through 74e, 76a through 76e, 78a through 78e, and 80, respectively. Conductors 72, collectively, are dressed together to form a signal cable 82, while conductors 74 collectively, 76 collectively, 78 collectively, and 80 are dressed together to form a signal cable 84. Cables 82 and 84 are merged together into a single signal cable 86 (see FIG. 6), which connects sensor assembly 58 to processor/pump module 16.

As with conductors 36, 38, and 40, conductors 72, 74, 76, 78, collectively, and 80 can be either electrical conductors or optical fibers. That is, the IR sources 62, collectively, and the IR detectors 64, 66, 68, collectively, and 70 may be located either within sensor assembly 58 itself, in which case the conductors are electrical conductors and carry electrical signals between processor/pump module 16 and sensor assembly 58, or within processor/pump module 16, in which case the conductors are optical fibers and carry infrared radiation between processor/pump module 16 and sensor assembly 58.

IR radiation generated by IR sources 62, collectively, is directed through peritoneal tissue 52, and thus the blood flowing through the tissue, to detectors 64, 66, 68, collectively, and 70 located across from the IR sources. As in the previous embodiment, each source or detector may have associated with it a narrow band filter, so that each optical source and the detectors associated with it in a given array operate in only a discrete narrow band of IR radiation. The IR radiation detected by detectors 64, 66, 68, collectively, and 70 is, of course, affected by its interaction with tissue 52 and the blood flowing therethrough. Consequently, by analyzing the output signals from the detectors, it is possible to derive information about the blood flowing through tissue 52. Preferably, although not necessarily, selected sensor/detector pairs are used for different measurement techniques, such as, for example, infrared transmittance, infrared reflectance, and infrared scattering. Thus, the output signals from the individual detectors can be processed differently to obtain different characteristics of the blood being measured.

Alternative Sensor Configuration

Figure 9:
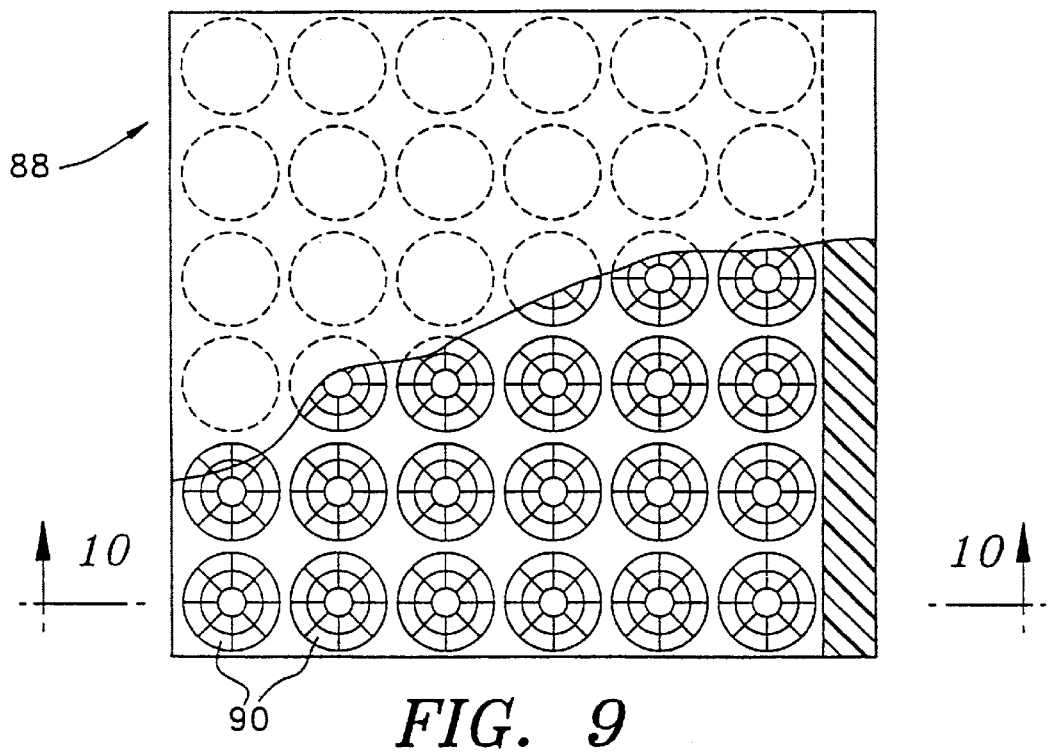
FIG. 9 illustrates a third embodiment of the invention, partially broken away, showing an arrangement of individual photocells in a rectangular array.
Figure 10:
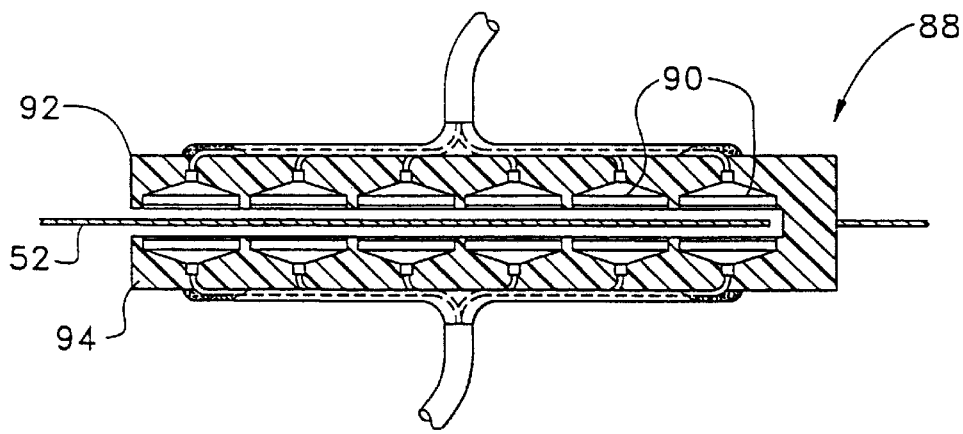
FIG. 10 is a sectional view of the sensor shown in FIG. 9, taken along the lines 10—10 in FIG. 9.

A third embodiment 88 of sensor assembly is illustrated in FIGS. 9 and 10. In those figures, sensor assembly 88 comprises a generally rectangular array of source/detectors 90 disposed on opposite halves 92 and 94 of the sensor assembly, with each half being on opposite sides of a vascular membrane 52. Source/detectors 90 are preferably, although not necessarily, arranged opposite one another on respective halves 92 and 94, so that the array on one half is substantially in alignment with the array on the other half.

Figure 11:
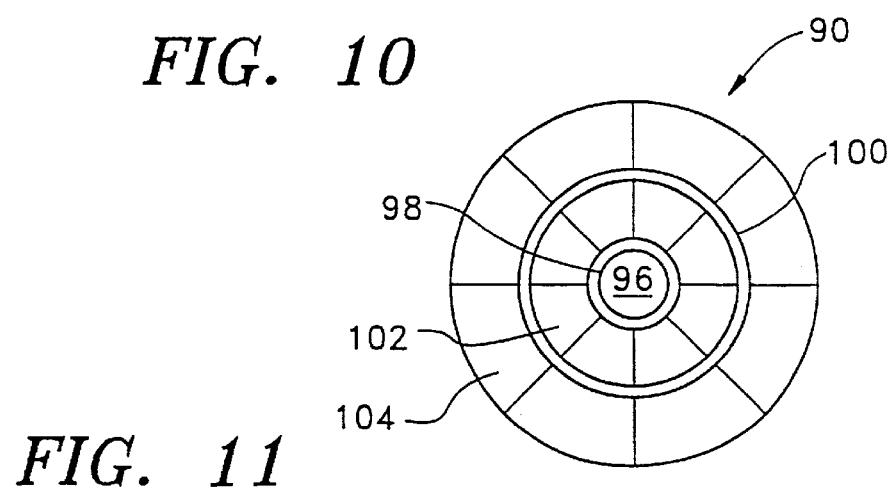
FIG. 11 is an enlarged plan view of an individual photocell from the array shown in FIG. 9.

An individual source/detector 90 is illustrated in more detail in FIG. 11. Source/detector 90 is generally circular, and at its center portion contains a source segment 96, from which infrared radiation is emitted. An inactive buffer ring 98 surrounds source segment 96. A second inactive buffer ring 100 is radially spaced from and surrounds buffer ring 98. Buffer rings 98 and 100 are inactive in the sense that they neither emit nor respond to IR radiation. The portion of source/detector 90 between buffer rings 98 and 100 is divided into a plurality of detector segments 102, each of which is associated with a narrow band filter so that it responds to a selected band of radiation. A linearly-variable filter can be used, for example. In this manner, each detector segment 102 operates in only a discrete narrow band. A second plurality of detector segments 104 is located radially outward of buffer ring 100, each of which is also associated with a narrow band filter so that it, too, responds to a selected band of radiation.

It will be appreciated that a single source/detector 90 can operate to measure both reflected and scattered IR, or a single pair of source/detectors 90 can operate to measure reflected, scattered, and transmitted light over a plurality of discrete radiation bands.

Figure 12:
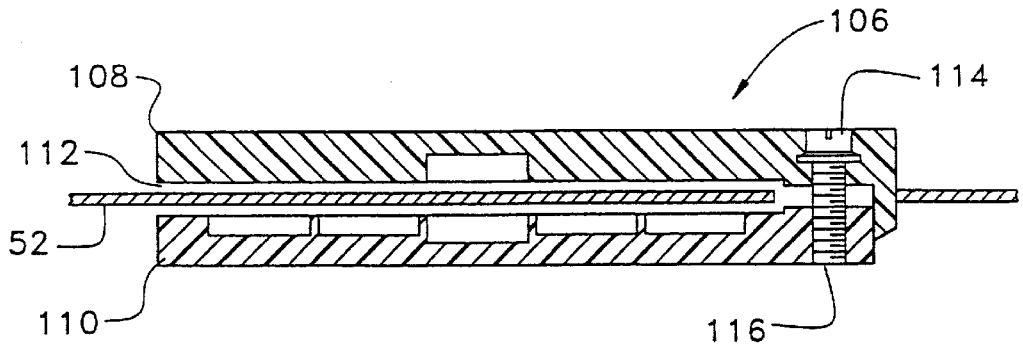
FIG. 12 is a fourth embodiment of the invention, in cross-sectional view.

FIG. 12 illustrates an embodiment 106 of a sensor assembly similar to those shown in FIGS. 7 and 10, except that the two halves 108 and 110 are not spaced apart by a fixed distance, as are the halves of the detectors in FIGS. 7 and 10. Instead, the halves 108 and 110 are movable toward and away from each other, and the gap 112 may be adjusted by means of adjusting screws 114. Preferably, the head portion of screw 114 is made captive, but freely rotatable, in one half, such as half 108. The shank portion of the screw is received in a threaded bore 116 in the opposite half. Thus, by rotating screw 114, the width of the gap 112 between halves 108 and 110 can be easily adjusted for optimum spacing of the individual sources and detectors relative to the vascular membrane 52.

Oxygenation and Tissue Perfusion Monitoring

Figure 13A:
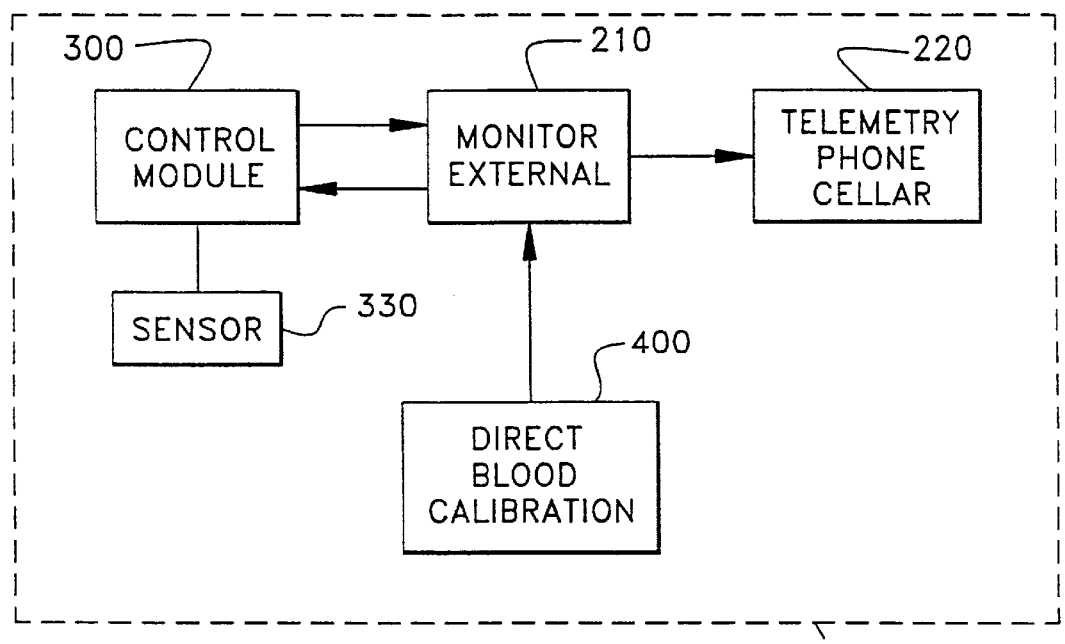
FIG. 13a illustrates a functional block diagram of an implantable blood constituent sensor module with communication means shown in conjunction with extracorporeal receiving, calibration, and communication modules.
Figure 13B:
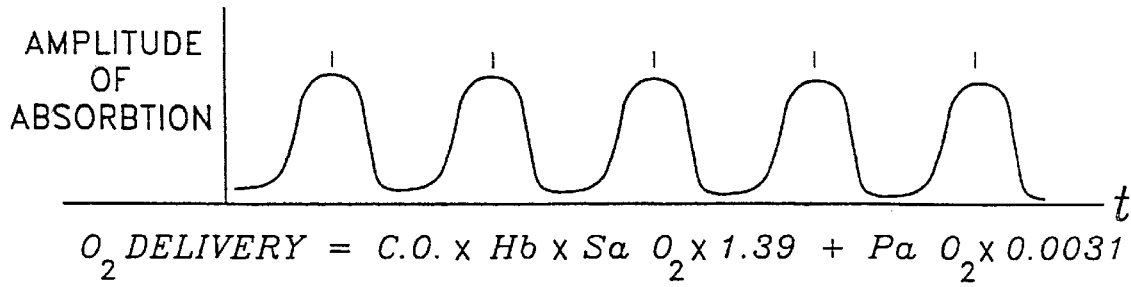
FIG. 13b illustrates a typical oxygen delivery process monitored according to a preferred embodiment of the present invention.

FIG. 13b illustrates this concept can be summarized using the following equations:

A. Oxygen delivery=cardiac output×oxygen saturation (%)×hemoglobin concentration (gm/dl)×1.39+partial pressure of oxygen (PaO2)×0.0031

B. Cardiac output=heart rate×stroke volume

Cardiac output is a measurement of blood flow (liters/minute) and can be defined as the heart rate times the stroke volume. The stroke volume is the amount of blood ejected with each beat of the heart and is influenced by th amount of blood returning to the heart, the state of contractility of the heart muscle, and degree of afterload or impedance to forward blood flow. (72 bts/min×80 ml/bt=5,760 ml/min). Heart rate can be measured by counting the plethysmograph pulse wave as shown in FIG. 13b.

Figure 13C:
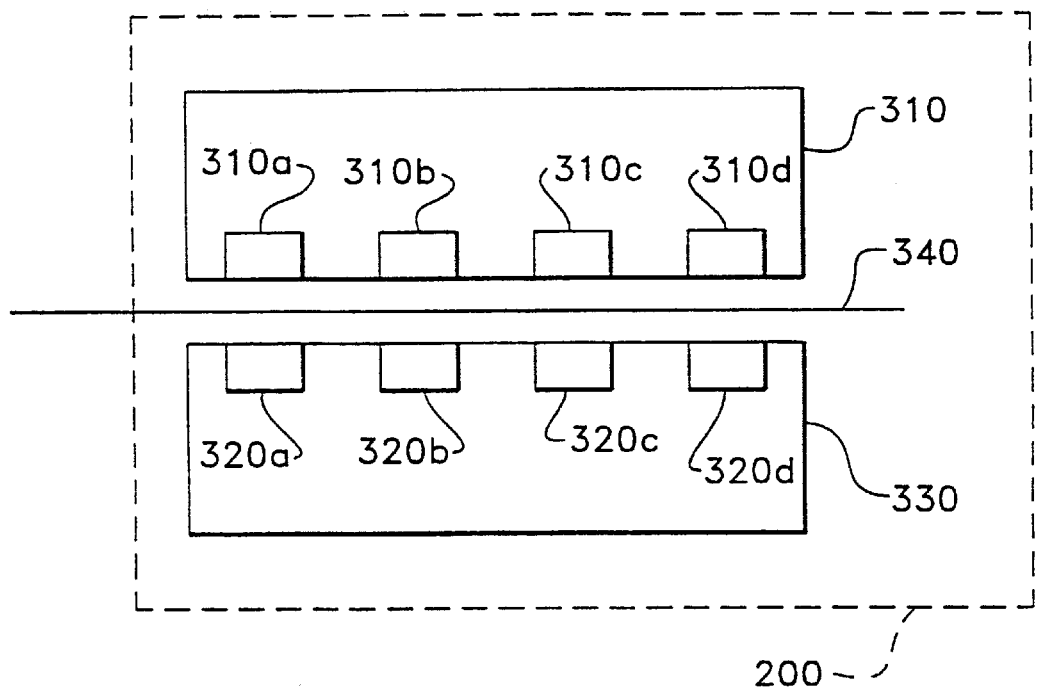
FIG. 13c illustrates an implantable oxygen sensor module having at least one pair of detector and sensor elements according to a preferred embodiment of the present invention.
Figure 13D:
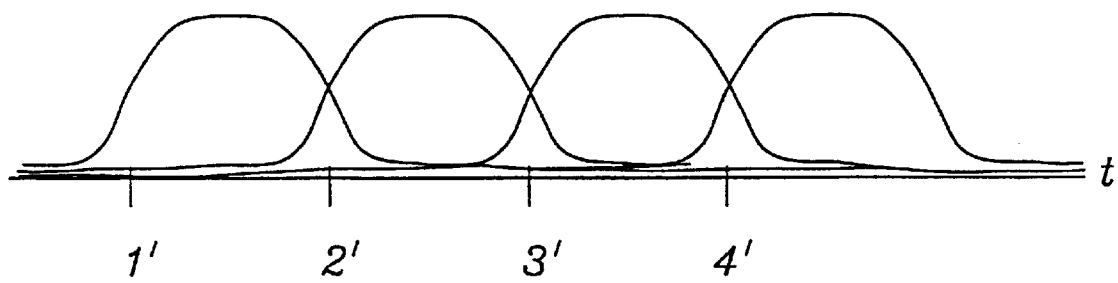
FIG. 13d illustrates a plethysmograph of a plurality of pulse waves through a vascular membrane at a specific rate as would be measured by at least two pairs of the detector and sensor elements shown in FIG. 13c.

Stroke volume can be estimated by analyzing the plethysmograph pulse wave illustrated in FIG. 13d including the maximum amplitude, the area under the curve, the rate of upstroke, and the velocity of wave propagation according to standard processing techniques. Current research is correlating pulse wave analysis with invasive monitoring such as Swan Ganz catheters and transesophageal echocardiography. Current pulse oximeter technology displays a pulse wave reflecting the volume of blood perfusing the tissue between the source and detector. Pulse detection algorithms evaluate the changes in light attenuation across a vascular tissue (photoplethysmography). The optical path length of the diastolic tissue bed and the optical path length of the systolic tissue bed is measured. The difference between the two is the optical path length of light being affected only by arterial blood. The microprocessor continually calculates the ratio of light absorption associated with both wavelengths of light emitted by the two source diodes. With diminished blood flow, conventional pulse oximeters increase the gain on the signal with no attempt to measure blood flow or pulse wave velocity. With sufficient gain on the signal and noise rejection algorithms, an accurate oxygen saturation measurement can be maintained despite a fall in tissue blood flow to less than 10% of baseline. Some commercially available pulse oximeters display the signal gain required (2×, 4×, 8×, etc.) to maintain a normal amplitude plethysmograph waveform and an accurate hemoglobin oxygen saturation reading. Analysis of the raw signal that produces the pulse wave includes the maximum amplitude, the area under the curve, the rate of upstroke, and the velocity of wave propagation. This raw signal data can be used to estimate the stroke volume per beat of the heart (volume of blood ejected per beat). The velocity of wave propagation can be measured using two or more source/detector pairs in series such that the pulse wave is detected with a slight time delay at the second pair and an additional time delay at the third. Since the distance between the sensor pairs is known and fixed, a pulse wave velocity can be calculated. The total combined analysis of the pulse wave will be used to estimate stroke volume and therefore an on-line estimate of cardiac output.

The amount of radiation absorption and scattered is significantly diminished by using a thin translucent vascular membrane as the optical interface. A higher signal to noise ratio is found compared to non-invasive pulse oximetry techniques.

C. Oxygen content within the blood=hemoglobin oxygen saturation (%)×hemoglobin concentration (gm/di)× 1.39+partial pressure of oxygen (PaO2)×0.0031

Hemoglobin oxygen saturation reflects the sigmoidal shaped dissociation curve in which hemoglobin is 98% saturated or greater when the partial pressure of oxygen exceeds 100 mm Hg. Saturation slowly falls such that hemoglobin is 95% saturated at an oxygen partial pressure of 60 mm Hg. Below this partial pressure, oxygen saturation falls dramatically. Commercially available pulse oximeter technology provides this information accurately and reliably.

Infrared spectroscopy is able to accurately measure blood hemoglobin concentration. Since 1.39 milliliters of oxygen can bind to each gram of hemoglobin, the total oxygen content of the blood can therefore be measured using optical means. The amount of oxygen dissolved in the plasma is negligible (partial pressure of oxygen (PaO2)×0.0031) and of little clinical significance.

The purpose of the implantable oxygenation, hemoglobin, and perfusion sensor is to obtain frequent objective data on patients with chronic illnesses such as heart failure and respiratory failure. Patients would be monitored for changes in hemoglobin oxygen saturation (pulse oximeter), hemoglobin concentration (infrared measurement), and changes in tissue perfusion (analysis of the photoplethsmograph waveform) for the purpose of detecting cardiovascular decompensation early so that the physician can manage the problem as an outpatient. Visits to the emergency room and admissions to the ICU would significantly diminish. Data from the sensors will be stored within a memory chip and reviewed by the physician during an office visit or over the phone. In one embodiment, the physician would be notified automatically if data changed significantly from the individual patient's normal pattern. Typically, patients wait until significant cardiovascular decompensation has produced overt symptoms requiring admission through the emergency room to the ICU. With this implantable sensor, physicians will be able to detect early decompensation and institute corrective therapy as an outpatient. Data stored in the memory chip will provide the clinician with the natural history of the disease process. The physician will be able to titrate medical therapy based on objective numbers and conclude from the data the benefits incurred by this therapy. All of the major determinants of oxygen delivery to the tissues can be measured with this sensor. For example, a patient develops heart failure and pulmonary edema following a myocardial infarction. Once stabilized in the ICU a sensor would be implanted under local anesthesia and data collected on-line. Once discharged from the hospital, the sensor would monitor the patient for significant changes in oxygenation, perfusion, hemoglobin concentration, and cardiac arrhythmia. If no significant changes occur, data would be stored in a memory chip and downloaded for physician interpretation during the patient's routine office visit. Medications that improve cardiac contractility and improve tissue blood flow could be titrated to objective endpoints rather than to vague patient symptoms.

Alternate clinical uses for this optical technology include integration of the output signal with an internal cardiac defibrillator (ICD). Patients are implanted the ICD following a near death experience due to a serious ventricular arrhythmia of the heart. Unfortunately, the electrocardiogram algorithms programmed into the ICD are unable to differentiate a life threatening arrhythmia from noise in certain cases. It is estimated that inappropriate defibrillation occurs 30% of the time. Using the implantable photoplethsmograph sensor (pulse oximeter), tissue blood flow data can be integrated with the algorithm for defibrillation. Both the ECG and tissue blood flow have to agree that a life threatening arrhythmia is present before defibrillation.

Closed-loop feedback with a programmable pacemaker provides a means to increase/decrease the heart rate and fine tune the timing intervals of a pacemaker to more physiologically meet the oxygenation and perfusion needs of the tissues during various levels of physical activity. The sensor would be placed on around a central vein returning to the right heart.

Measurement of venous oxygen saturation reflects the adequacy of cardiac output and oxygen delivery to the peripheral tissues. During exercise, blood flow increases several fold to the muscles and other tissues. When the heart is paced at a fixed low rate, the tissues extract a greater percentage of the oxygen delivered. Low venous saturation suggests the need to increase oxygen delivery by increasing the cardiac output and by increasing the oxygen carrying capacity of the blood (transfusion red blood cells, iron therapy). Decreasing venous oxygen saturation would signal the pacemaker to increase the heart rate and to optimize the timing intervals between atrial and ventricular contraction thus regulating the cardiac output of the heart. Once the oxygen debt was satisfied, the heart rate would slowly return to baseline values. In this way, the pacemaker would compensate for an increased demand for oxygen in the peripheral tissues.

FIG. 13a illustrates a functional block diagram of a blood oxygen and perfusion monitoring and control system 200 comprising an implanted sensor 330 (shown in FIG. 13c) and an implanted control module 300 (not shown in detail) which is in communication with an extracorporeal monitor 210. The extracorporeal monitor 210 is in communication with a direct blood calibration module 400 (explained in detail below) and other communication systems such as, but not limited to, a cellular telephone 220, an emergency medical warning system (not shown), or a hand held monitoring device (shown in FIG. 18b).

The blood oxygen perfusion monitoring and control module 200 is surgically implanted in a patient where it is employed to measure, control, monitor, and report measured hemoglobin oxygen saturation and tissue perfusion. As shown in FIG. 13b, measured blood oxygen is represented as the amount of oxygen delivered to the blood on a pulse by pulse basis as the blood is pumped by the heart. The amount of blood oxygen delivered to the body can be represented according the following formula:

$$O_2 \text{ (Delivered)} = * \text{ Hb} * SaO_2 * 1.39 + PaO_2 * 0.0031,$$

where,

C.O.=Cardiac Output=Heart rate×stroke volume liters/mn,

Hb=Hemoglobin concentration mg/dl, $SaO_2$=Hemoglobin oxygen saturation %, 1.39=a constant representing 1.39 ml of oxygen bound to one gram of Hemoglobin, $PaO_2$=partial pressure of oxygen dissolved in plasma, and 0.0031=a constant representing the amount of oxygen dissolved in plasma.

The blood oxygen is measured as an estimate of oxygen according to the pulsatile perfusion of the blood through a vascular interface. It is to be understood that the vascular interface can be, but is not limited to, an artery, a vein, a vascular membrane, or vascular tissue. The oxygen measurement is acquired according to standard pulse oximetry described above. In a preferred embodiment of the present invention, oxygen is measured by the implanted control module 300 and at least one paired sensor assembly 330 (shown in FIG. 13c).

FIG. 13c illustrates an embodiment of the sensor assembly 330 assembly similar to those shown in FIGS. 7, 10 and 12. However, the two halves 310 and 320 have linearly arrayed elements that are spaced apart by a distance defined by a vascular membrane 340. The linear arrays are paired together to form a plurality of paired arrays as may be required to acquire a plethysmographic representation of the pulsatile flow of oxygenated and reduced hemoglobin passing through the vascular membrane 340. A single paired array is required to produce a plethysmograph as shown in FIG. 13b, and, multiple arrays, are required to measure a velocity of the pulse wave.

In the embodiment of sensor 330 illustrated in FIGS. 13c, the optical sources and optical detectors may be infrared (IR) sources and IR detectors, although radiation from infrared through the visible spectrum may be employed without departing from the invention. In the figures, individual IR sources 310a–d and individual IR detectors 320a–d are grouped together in pairs forming the paired array 330. A plurality of paired arrays will also comprise an plurality of IR sources and IR detectors respectively. The individual IR sources 310a–d may be miniature infrared diodes located, in the illustrated embodiment, on one side of the vascular membrane 340. IR sources 310a–d are driven by signals generated in the control module 300 and transmitted to the IR sources 310a–d via conductors (not shown). Similarly, output signals from individual detectors 320a–d are transmitted to the control module 300 via separate conductors (not shown).

Each IR source 310 and detector 320 may have associated with it an optical filter (not shown) or a time based or encoded discriminator (not shown) for selectively emitting and detecting the selected bands of radiation emitted for detecting blood oxygen saturation.

With this embodiment, the IR sources 310 and detectors 320 are arranged diametrically opposite each other to detect light transmitted through the vascular membrane 340.

It is important to note that, although this embodiment of the invention is described using a single array of paired IR sources and associated detectors, that precise configuration is not crucial to the invention. In fact, the invention may be implemented, for example, using a plurality of paired arrays for detecting reflected, scattered, and transmitted IR radiation.

FIG. 13d shows a plethysmographic representation of pulsatile blood oxygen perfusion when four paired arrays are employed.

The implanted control module 300 preferably incorporates a pulse oximeter module (not shown) for producing perfusion data (as shown in FIG. 13d). Also incorporated in the control module 300 is a processor module (not shown) for analyzing the perfusion data and for producing a control signal that is communicated by the control module 300 to a blood oxygen regulating device such as, but not limited to, a pacemaker or defibrillator.

Figure 14:
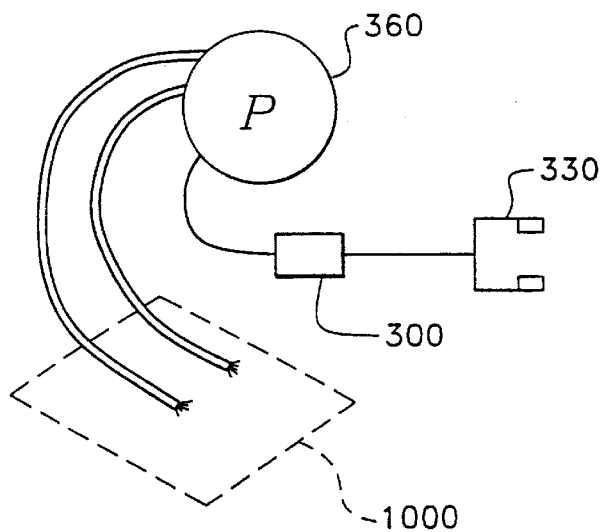
FIG. 14 is a schematic representation of a device for controlling the blood oxygen according to a preferred embodiment of the present invention.

FIG. 14 is an illustration of a preferred aspect of the invention showing a control module 300 having a sensor 330 for measuring perfusion data to determine the level of blood oxygen. The sensor 330 as explained above employs at least two selected bands of frequencies to produce detected signals corresponding to oxygenated hemoglobin levels which are analyzed by the processor module (not shown) of the control module 300.

The control module 300 also incorporates a communication module (not shown) for communicating control information to an implanted pacemaker 360. The pacemaker 360, in response to the control information received from the control module 300, regulates the heart 1000 (shown for illustrative purposes) to pump blood as required to produce a desired blood oxygen level. The control module 300 controls blood oxygen by regulating the pacemaker to control heart rate and timing of atrial and ventricular contraction according to stored blood oxygen values programmed into the control module 300. Programmed blood oxygen values are stored in the control module 300 through its communication module. An extracorporeal communication device (shown in FIG. 18a) is used to control and calibrate the control module 300 which is explained in detail below.

Figure 15A:
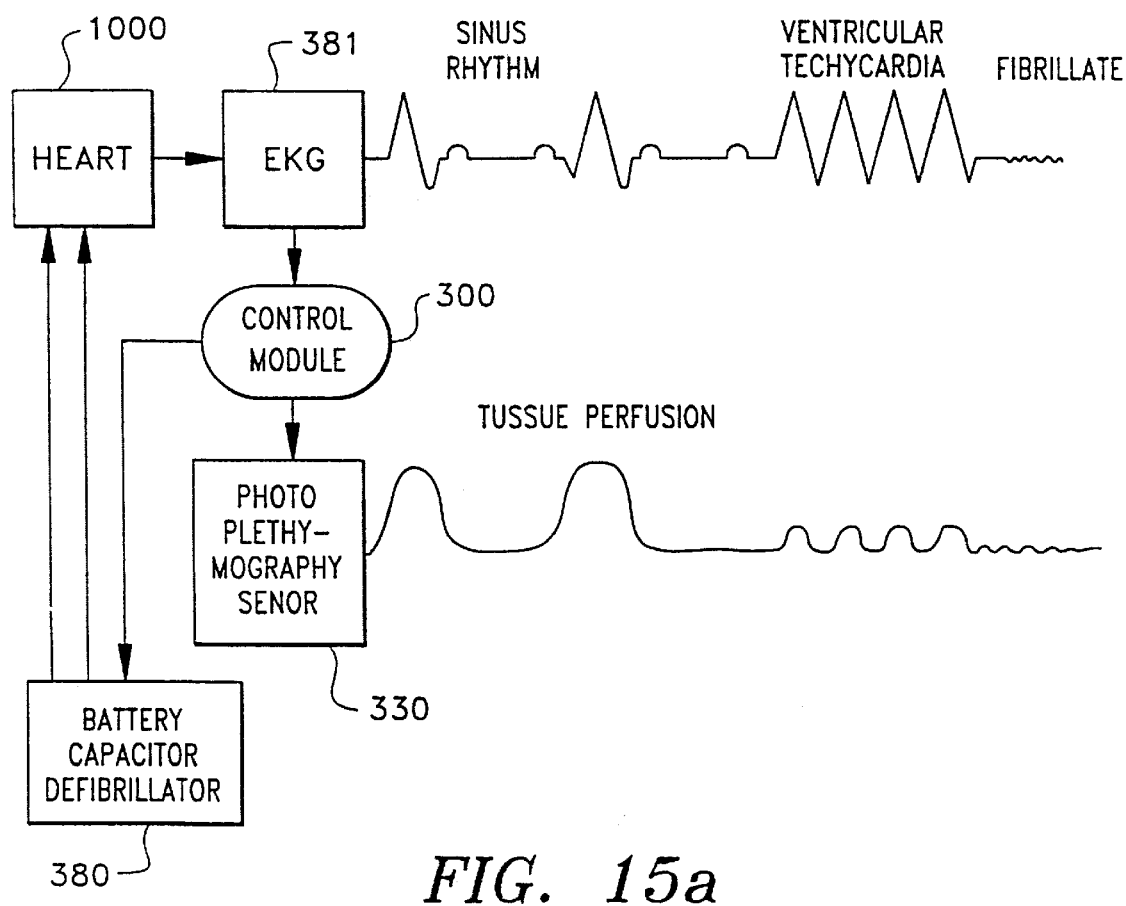
FIG. 15a is a schematic representation of a device for controlling the level of blood oxygen according to another preferred embodiment of the present invention.

FIG. 15a is an illustration of another preferred aspect of the invention showing a control module 300 having a sensor 330 for measuring perfusion data to estimate quantity of blood delivered per beat to the tissues. The control module 300 incorporates a communication module (not shown) for communicating control information to an implanted defibrillator 380. The defibrillator 380, in response to the control information from the control module 300 and its own internal EKG system 381 (shown for illustrative purposes) will regulate the heart 1000 (shown for illustrative purposes) to prevent inappropriate in other words the discharge of the internal defribulator.

It is known that an internal defibrillator will at times inappropriately defibrillate irregular heart beat patterns. When this occurs the level of blood oxygen can be severally affected. To prevent this condition, the level of blood oxygen measured by the control module 300 is used to confirm proper heart function. Because the control module 300 and sensor 330 use photo-plethysmography to measure pulsatile perfusion, actual defibrillation can be detected as an instantaneous loss of blood oxygen.

In FIG. 15a the electrical activity of the heart normal sinusrhythm with satisfactory tissue perfusion and oxygenation noted on the plethysmography waveform. As the trace pressures the cardiac rhythm degenerates into ventricular tachycardia and then ventricular fibrillation. The tissue perfusion and oxygenation also deteriorates such that pulsatile flow is lost.

Figure 15B:
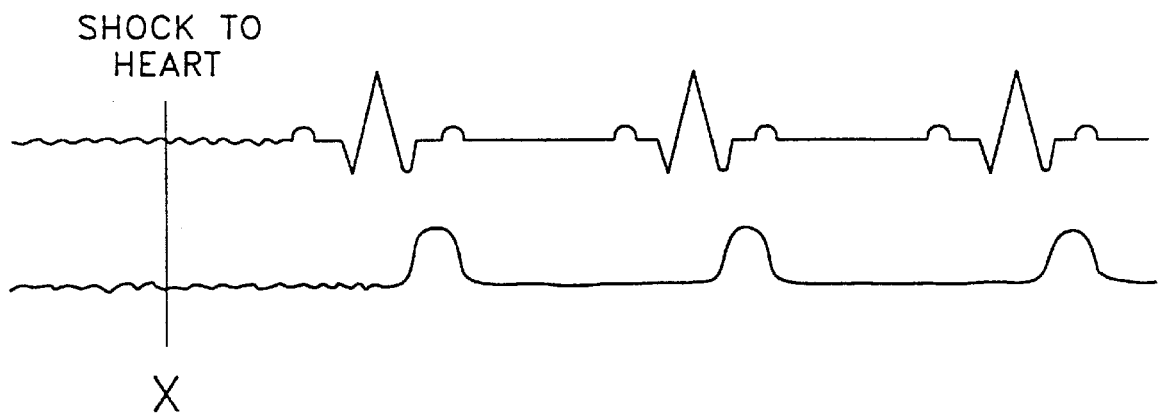
FIG. 15b is a schematic representation of vascular tissue plethysmography and ECG fibrillation according to a preferred embodiment of the present invention.

FIG. 15b represents a continuation of the ventricular fibrillation trace and lack of pulsatile tissue bound flow at timex. The internal defibrillation produces an electrical shock that converts the cardiac rhythm to normal with satisfactory pulsatile tissue blood flow.

FIG. 15a illustrates vascular tissue plethysmography with a simultaneous and EKG recording of the heart. Therefore, the use of perfusion data to control blood oxygen by preventing cardiac defibrillation is a very important feature of the invention. This feature provides increased assurance that blood oxygen will be maintained consistently without disruptions caused by inappropriate heart fibrillation.

Specific Blood Constituent Monitoring, Control and Reporting System

Naturally, it should be understood that, although embodiments using different groupings of sources and detectors have been described for the measurement and control of blood glucose and blood oxygen, the invention is not in any way limited to either a specific number of source/detector groupings or blood constituents, nor is it absolutely necessary that the sources and detectors be arranged in specific configurations.

Figure 16A:
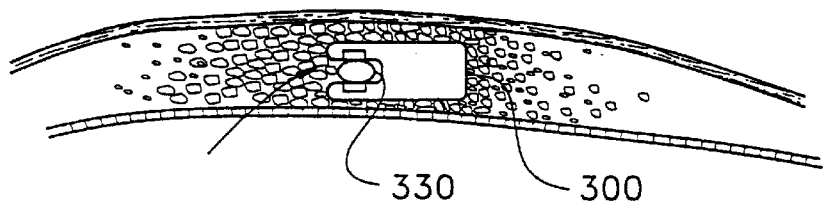
FIG. 16a is a schematic representation of an infrared sensor according to a preferred embodiment of the present invention.

FIGS. 16a is a schematic representation of an infrared sensor 330 and its control module 300 equipped with a communication module (not shown) according to a another preferred embodiment of the present invention. The control module 300 and sensor 330 are implanted into the body subcutaneously just below the skin. The sensor 330 is placed about a vein, an artery or inserted into vascular tissue allowing it to measure and control selected blood constituents. The control module 300 through its communication module can communicate the measured level of blood constituent extracorporeally by means of its communication module to devices such as, but not limited to, an external monitoring and warning device, or a telecommunication network.

Figure 16B:
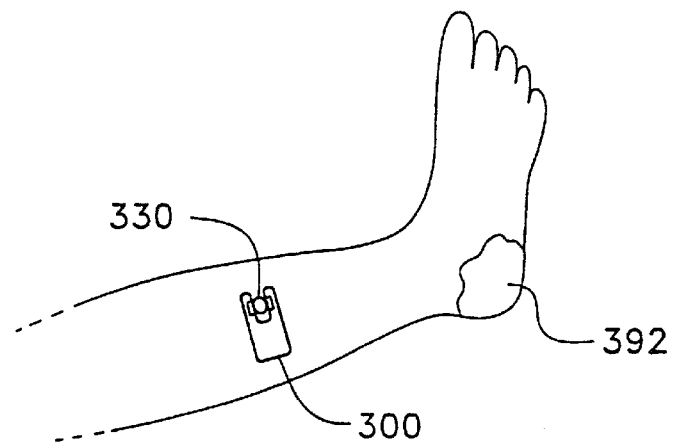
FIG. 16b is a schematic representation of the infrared sensor shown in FIG. 16a used to measure and control a medicinal blood constituent such as an antibiotic.

FIG. 16b is a schematic representation of the infrared sensor 330 shown in FIG. 16a used to measure and control a medicinal blood constituent such as an antibiotic which is used to treat a localized infection 392 (shown for illustrative purposes). It is to be understood that this invention is not limited to this embodiment, but may be used to deliver, measure and control any medicinal blood constituent such as, but not limited to, chemotherapy and cardiac medications. In addition, the measured level of medication in the blood can be monitored extracorporeally by a monitoring device or provide to a remote location by means of an external communication system adapted to a telecommunication network.

In addition, to controlling blood constituents, the sensor 330 and control device 300 can be used to measure and report blood constituent levels extracorporeally to remote monitoring equipment. For example, blood constituents such as tumor markers including, but not limited to, prostate specific antigen (PSA) for detecting prostate cancer and colon embryonic antigen (CEA) for detecting colon cancer, can be continuously monitored safely and conveniently without the need and inconvenience of constantly drawing blood and laboratory testing. By measuring these tumor markers on a daily basis, recurrence of tumor will be detected early prior to spread throughout the body. This can be accomplished by selecting the appropriate optical sensors and detector and operating bandwidths for interaction with each specific blood constituent.

For example and as explained above, blood oxygen can be measured through oxygenated hemoglobin with two pairs of sensors and detectors operating at 660 nanometers and 940 nanometers for detecting oxygenated and reduced hemoglobin.

Implantable Optic Sensor Interface (IOSI)

Figure 17A:
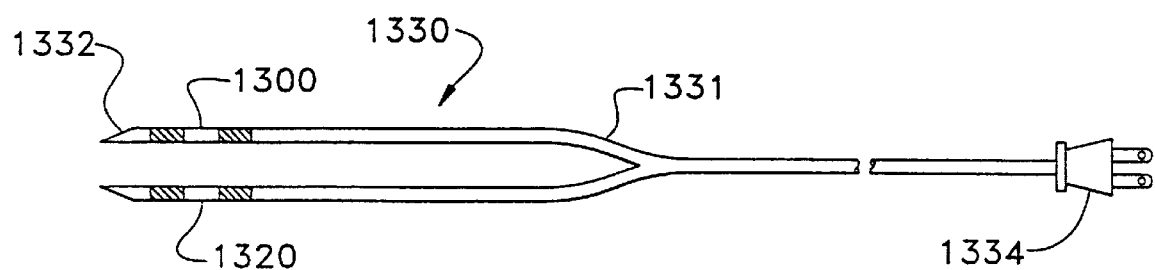
FIG. 17 is a schematic representation of an infrared sensor according to another preferred embodiment of the present invention.
Figure 17B:
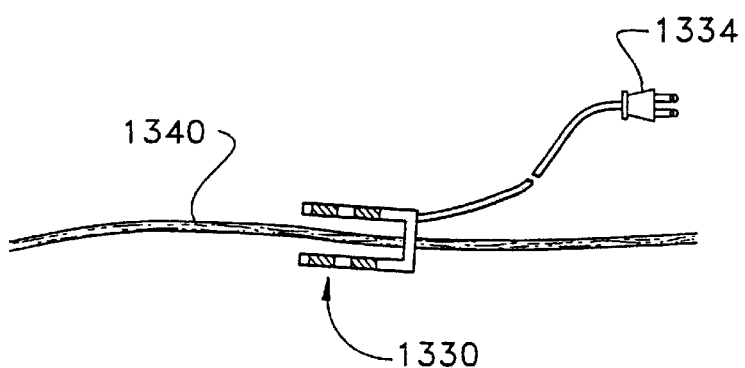
Figure 17C:
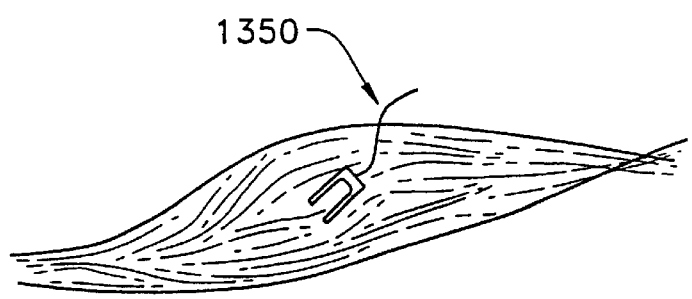

FIG. 17a is a schematic representation of an infrared sensor 1330 according to another preferred embodiment of the present invention. The sensor 1330 is shaped like a tuning fork and is implanted surgically into vascular tissue. The shape facilitates insertion and retention into vascular rich tissue such as a muscle or vascular membrane as shown in FIGS. 17b and 17c. The sensor has two parallel arms 1320 joined at one end and separated from each other by a fixed distance. Each arm has a pointed tip 1332 at its other end for piercing the tissue. As the sensor is inserted into the tissue a vascular interface 1334 is formed between the arms 1310,1320. The arms 1310,1320 have at least one electromagnetically sensitive array comprising optical sources and detectors for illuminating the vascular interface 1340 and detecting a desired blood constituent described above.

FIG. 18a is an illustration of an extracorporeal calibration and communication module 410. FIG. 18b is an illustration of a hand held monitor, display and communication unit 450 for use in connection with implantable blood constituent sensors and control modules described above. The calibration and control module 410 communicates with a communication module (not shown) associated with the implanted control module 300, providing calibration data and extracorporeal display and reporting of the measured data produced by the control module 300.

The extracorporeal calibration and communication module 410 communicates calibration data directly to the implanted control module 300 allowing precise calibration of the measurements made by the control module 300 and its sensor 330. Calibration data is produced by the extracorporeal calibration and communication module 410 by commercially available methods such as glucose oxidase reagent strips 420.

The communication module 410 and the control module 300 are equipped with commercially available communication means adapted for intercorporeal communication.

FIG. 18c is a functional block diagram showing the operation of an implantable device according to the invention in communication with the extracorporeal calibration and communication module shown in FIG. 18a.

Extracorporeal Calibration and Communication Modules

As already noted, processor/pump module 16 contains an electronic microprocessor and associated electronic circuitry for generating signals to and processing signals from sensor assembly 14 and for generating control signals to the insulin pump itself. The microprocessor is preferably programmed to execute algorithms to perform multispectral correlation, and matched digital bandpass filtering to remove low frequency bias and high frequency noise. Such algorithms are well-known to those skilled in the art, and need not be described in detail. Moreover, the invention is not limited to any specific algorithm; rather, any algorithms suitable for performing the desired multispectral correlation and filtering functions may be used without departing from the invention. It should also be noted that, while the present invention provides accurate glucose level measurements, accurate measurement is not crucial to the control of the insulin pump 16. In a manner similar to the way a house thermostat operates, the pump 16 can be controlled to release a fixed quantity of insulin until the glucose levels falls below a preselected level. Thus, any algorithm capable of such control is within the scope of the invention. The algorithm may also control insulin pump 16 to release a glucagon bolus, (1 mg of glucagon, when blood glucose levels trend below 60 mg/dl will increase the blood glucose level above 150 mg/dl).

Processor/pump module 16 may also contain a telemetry transmitter to transmit sensor data to an external processor and external insulin pump. Insulin can be injected subcutaneously or into a subcutaneous infusaport for delivery into the peritoneal cavity or into a portal vein.

Processor/pump module 16 may also consist of a telemetry receiver for external calibration. If recalibration is necessary, the system 10 may be recalibrated externally by comparison to a weekly or monthly finger stick blood glucose measurement, such as, for example, using calorimetric assay of a glucose oxidase/hydrogen peroxide reaction using standard techniques. The absolute glucose amount from the external calibration measurement can then be telemetered to the processor for calibration.

Alternatively, each source of radiation may consist of multiple discrete bands of light with a unique temporal or frequency modulation, allowing discrimination of the different spectral bands.

Alternatively to providing a narrow band filter for each detector, the different spectral bands from the sources are each modulated in a unique temporal or frequency fashion, allowing for discrimination of the different spectral regions and obviating the need for narrow band filters.

In another embodiment, source 310a (or 310b, 310c, or 310d) may consist of multiple LEDs or multiple laser diodes, each of a different wavelength spaced identically collinear or spaced very closely so that each wavelength has substantially the identical optical path and interacts with substantially identical tissue. The detector 320a, b, c, or d detects light from each individual wavelength from source 320a, b, c, or d, respectively.

The processor discriminates amongst the different wavelengths by having each wavelength pulse at a different frequency or at a different time. As the processor can discriminate amongst the different wavelengths by either different frequency or temporal information, narrow wavelength filters 46a. 48a, and 50a are unnecessary in this embodiment. Multiple sources and multiple detectors provide redundancy or alternatively the ability to measure different chemical species, although in many cases a single source and detector is adequate. The operation of the sensor is otherwise the same as described in the previous embodiment.

Fourier Transform Infrared Spectroscopy (FTIR) Analysis

Using commercially available Fourier transform infrared spectroscopy (FTIR) analysis, it is possible to correlate the sensor output data with blood glucose levels, blood fatty acid levels, and blood amino acid levels.

The present invention may be embodied in other specific forms without departing from the spirit or essential attributes thereof and, accordingly, reference should be made to the appended claims, rather than to the foregoing specification, as indicating the scope of the invention.

What is claimed is:

1. A device for sensing in-vivo the level of at least one constituent of blood within mammalian vascular tissue, comprising at least one implantable source of radiation from infrared through visible light, the source emitting radiation in at least two selected frequency bands, the at least one implantable source of radiation being arranged to direct the radiation at blood within the tissue and being located out of direct contact with the blood, the radiation being affected by direct interaction with the blood, at least one implantable detector adapted to be located out of direct contact with the blood and adapted to be located with respect to the tissue to receive radiation affected by the direct interaction with the blood, means associated with the source and the detector for deriving from the detector an output signal containing spectral information about the blood within the at least two selected frequency bands, and a processor for processing the output signal to derive the level of the blood constituent.

2. A device according to claim 1, wherein the level of the blood constituent is the degree of oxygen saturation in hemoglobin.

3. A device according to claim 2, further comprising a pacemaker connected to the processor, the processor communicating the derived degree of oxygen saturation to the pacemaker to regulate heart rate and time of atrial and ventricular contractions in accordance with a predetermined level of blood oxygen saturation.

4. A device according to claim 2, further comprising an implantable defibrillator connected to the processor, the processor communicating the derived degree of oxygen saturation to the defibrillator to confirm heart function prior to activation of the defibrillator.

5. A device according to claim 1, wherein the blood constituent is blood glucose, and the selected frequency bands are selected to derive the level of blood glucose.

6. A device according to claim 5, further comprising an audible alarm which activates when the blood glucose level is determined by the processor to be in the hypoglycemic range.

7. A device according to claim 5, further comprising an insulin pump for dispensing doses of insulin in response to the level of blood glucose.

8. A device according to claim 1, wherein there are at least two detectors, and each detector has a filter which is transparent to a respective one of the selected frequency bands.

9. A device according to claim 1, further comprising a channel having an internal circumference around which are arranged the source and the detector, the channel being dimensioned to receive a blood vessel therein and to locate the vessel in proximity to the source and detector.

10. A device according to claim 1, wherein the at least one detector is located opposite the source and spaced therefrom by a distance sufficient to receive the tissue between the source and the detector.

11. A device according to claim 1, further comprising:
at least one optical fiber adapted for conveying radiation between the source and the tissue, or the tissue and the detector.

12. A device according to claim 1 wherein the processor is extracorporeal, the device further comprising a telemetry transmitter connected to the output signal for transmitting the spectral information about the blood extracorporeally to the extracorporeal processor.

13. A device according to claim 1, further comprising a telemetry transmitter connected to the processor for transmitting the derived level of the blood constituent to a phone.

14. A device for according to claim 1, further comprising:
a control device for administering a medicine in response to the level of the blood constituent.

15. A device according to claim 1, wherein the vascular tissue is a vascular membrane, and the emitted radiation from the source directly interacts with the membrane, and the detector receives radiation affected by the direct interaction with the blood.

16. A device according to claim 1, wherein the vascular tissue is a muscle and the emitted radiation from the source interacts with blood within the muscle, and the detector receives radiation affected by the direct interaction with the blood.

17. A device according to claim 1, wherein the spectral information is obtained by modulating the frequency bands of the source with respect to one another.

18. A device according to claim 1, wherein the source comprises a plurality of LEDs of selected wavelengths.

19. A device according to claim 1, further comprising a calibration device for receiving the level of the blood constituent from the processor and for periodically calibrating the level against measurement of the blood constituent obtained by another known technique.

20. A device according to claim 1, wherein the radiation source consists of a plurality of laser diodes.

21. A device for measuring and controlling the level of blood glucose in a mammal, comprising:

an implantable source and sensor module adapted for (i) directing radiation at blood within vascular tissue, (ii) sensing the radiation after it has interacted directly with the blood within the tissue, and (iii) generating an output signal representative of the direct interaction of radiation with the blood within the tissue, the source and sensor module comprising at least one implantable source of radiation from infrared through visible light which emits radiation in at least two selected frequency bands, the source and sensor module adapted to be located out of direct contact with the blood, and adapted to be located with respect to the tissue to receive radiation affected by interaction with the blood within the tissue, means associated with the implantable source and sensor module for receiving the output signal and deriving therefrom a spectral output signal containing spectral information about the blood within the at least two selected frequency bands, a processor responsive to the spectral output signal for performing spectral analysis of the spectral output signal and deriving therefrom a control signal related to the level of the blood glucose, and an insulin pump for dispensing doses of insulin in response to the control signal.

22. A method for sensing in-vivo the level of at least one constituent of blood within mammalian vascular tissue, the method comprising the steps of:

implanting in mammalian vascular tissue, and out of direct contact with blood to be analyzed, at least one implantable source of radiation from infrared through visible light, the source emitting radiation in at least two selected frequency bands, the at least one implantable source of radiation being arranged to direct the radiation at blood within the tissue, the radiation being affected by interaction with the blood, implanting at least one implantable detector located out of direct contact with the blood and being located with respect to the tissue to receive radiation affected directly by interaction with the blood, deriving from the detector an output signal containing spectral information about the blood within the at least two selected frequency bands, and processing the output signal to derive the level of the blood constituent.

23. A method for measuring and controlling the level of blood oxygen in a mammal comprising the steps of:

implanting extravascularly an implantable source and sensor module in the mammal, the source and sensor module including at least one source of radiation from the infrared through visible light, directing the radiation through vascular tissue using the at least one source of radiation, the radiation being affected directly by interaction with blood within the tissue, sensing the radiation after it has passed through the tissue and generating an output signal representative of the sensed radiation by using the sensor module, spectrally analyzing the output signal using a processor module and deriving therefrom a control signal representative of the level of the blood oxygen, and controlling the level of the blood oxygen in response to the control signal.

24. A method according to claim 23, wherein the controlling step is performed by controlling the function of a pacemaker.

25. A method according to claim 23, wherein the controlling step is performed by controlling the function of a defibrillator.

26. A method according to claim 23, wherein the implanting step includes implanting a source and sensor module comprising a plurality of detectors, each having associated therewith a filter transparent to a discrete narrow band of radiation, each detector providing an output signal representative of detected radiation in the narrow band, the detectors being located with respect to the tissue to receive radiation from the source affected by the tissue.

27. A method according to claim 23, wherein the implanting step includes implanting a source and sensor module comprising at least one source of radiation for emitting at least one selected band of radiation from infrared through visible light at the blood in the tissue, the radiation being affected by interaction with the tissue, and at least one detector adapted to receive the at least one selected band of affected radiation, each detector providing an output signal representative of the affected radiation.

28. A method according to claim 23, further comprising the steps of:

communicating the control signal representative of the level of the blood oxygen to an extracorporeal calibration module, and communicating calibration signals from the calibration module to the processor module for calibrating the control signal representative of the level of the blood oxygen, the calibration signals being obtained by another known technique.

* * * * *

UNITED STATES PATENT AND TRADEMARK OFFICE
CERTIFICATE OF CORRECTION

PATENT NO. : 6,122,536
DATED : September 19, 2000
INVENTOR(S) : Xiaoguong Sun, Jeffrey I. Joseph, Katherine D. Crothall It is certified that error appears in the above-indentified patent and that said Letters Patent is hereby corrected as shown below:

Title page, item [73] Assignee: "Animas Corporation, Malvern, PA." should read
"Animas Corporation, Frazer, PA and Thomas Jefferson University, Philadelphia, PA."

Signed and Sealed this

Tenth Day of April, 2001

*Attest:*

NICHOLAS P. GODICI

*Attesting Officer*   *Acting Director of the United States Patent and Trademark Office*